US012810990B2

(12) United States Patent
Voet et al.

(10) Patent No.: US 12,810,990 B2
(45) Date of Patent: Nov. 24, 2026

(54) METHOD AND SYSTEM FOR RADIATION TREATMENT PLANNING

(71) Applicant: Elekta, Inc., Atlanta, GA (US)

(72) Inventors: Peter Voet, Atlanta, GA (US); Chunhua Men, Atlanta, GA (US); Randy Larson, Atlanta, GA (US); Spencer Marshall, Brandon, FL (US)

(73) Assignee: Elekta, Inc., Atlanta, GA (US)

( * ) Notice: Subject to any disclaimer, the term of this patent is extended or adjusted under 35 U.S.C. 154(b) by 731 days.

(21) Appl. No.: 18/315,969

(22) Filed: May 11, 2023

(65) Prior Publication Data

US 2024/0379211 A1 Nov. 14, 2024

(51) Int. Cl.
*G16H 20/40* (2018.01)

(52) U.S. Cl.
CPC .................................. *G16H 20/40* (2018.01)

(58) Field of Classification Search
None
See application file for complete search history.

(56) References Cited

U.S. PATENT DOCUMENTS

| | | | |
|---|---|---|---|
| 6,064,203 A | 5/2000 | Bottomley | |
| 6,963,771 B2 | 11/2005 | Scarantino et al. | |
| 7,317,192 B2 | 1/2008 | Ma | |
| 8,492,735 B2 | 7/2013 | Brand | |
| 9,884,206 B2 | 2/2018 | Schulte et al. | |
| 10,737,114 B2 | 8/2020 | Gattiker et al. | |
| 10,835,760 B2 | 11/2020 | Kuusela et al. | |
| 2003/0219098 A1 * | 11/2003 | McNutt ................ | A61N 5/1031 378/65 |

(Continued)

FOREIGN PATENT DOCUMENTS

| | | |
|---|---|---|
| EP | 3681600 | 7/2020 |

OTHER PUBLICATIONS

Hindi et al., "A tutorial on optimization methods for cancer radiation treatment planning". American Control Conference (ACC). 2013, . (Year: 2013).*

(Continued)

*Primary Examiner* — Yi-Shan Yang
(74) *Attorney, Agent, or Firm* — Schwegman Lundberg & Woessner, P.A.

(57) ABSTRACT

A method of radiation treatment planning for a radiotherapy system, the method comprising: receiving a first reference objective and a second reference objective, each reference objective representing a goal to be achieved by the radiotherapy system, and the first reference objective comprising a reference dose to be delivered to a reference volume of an anatomical structure, optimising a set of parameters, according to the received first reference objective and the received second reference objective, the set of parameters relating to characteristics of radiation to be delivered by the radiotherapy system, wherein optimising the set of parameters comprises: optimising the set of parameters based on the first reference objective to obtain a dose-volume metric for the anatomical structure, and further optimising the set of parameters based on the second reference objective using the dose-volume metric as constraint, and generating a radiation treatment plan using the further optimised set of parameters.

11 Claims, 9 Drawing Sheets

(56) References Cited

U.S. PATENT DOCUMENTS

| | | | | |
|---|---|---|---|---|
| 2010/0104068 | A1 * | 4/2010 | Kilby | A61N 5/1031 378/65 |
| 2015/0202464 | A1 | 7/2015 | Brand et al. | |
| 2018/0304099 | A1 | 10/2018 | Li et al. | |
| 2021/0138267 | A1 | 5/2021 | Nord et al. | |
| 2021/0316157 | A1 | 10/2021 | Lynch et al. | |

OTHER PUBLICATIONS

Zhang et al., "Direct optimization of dose-volume histogram metrics in radiation therapy treatment planning". 2020. RaySearch Laboratories, Sweden. (Year: 2020).*

Elekta AB, "", Monaco Training Guide, Document ID: LTGMON0530, (2017), 1313 pgs.

Naccarato, Stefania, "Automated Planning for Prostate Stereotactic Body Radiation Therapy on the 1.5 T MR Linac", Advances in Radiation Oncology vol. 7 Issue 3, Oct. 19, 2021, 12 pgs.

"European Application No. 24175405.0, Extended European Search Report dated Dec. 10, 2024", (Dec. 10, 2024), 9 pgs.

Schlaefer, Alexander, "Stepwise multi-criteria optimization for robotic radiosurgery", Medical physics 35.5, (2008), 2094-2103.

* cited by examiner

METHOD AND SYSTEM FOR RADIATION TREATMENT PLANNING

FIELD

Embodiments herein relate to methods and systems for radiation treatment planning.

BACKGROUND

Radiotherapy or radiation therapy can be described as the use of ionising radiation to damage or destroy unhealthy cells in both humans and animals. The ionising radiation may be directed to tumours on the surface of the skin or deep inside the body. Common forms of ionising radiation include X-rays and charged particles. An example of a radiotherapy technique is referred to as Gamma Knife® or Leksell Gamma Knife® where a patient is irradiated using a number of lower-intensity gamma rays that converge with higher intensity and high precision at a targeted region (e.g., a tumour). Another example of radiotherapy comprises using a linear accelerator ("linac"), whereby a targeted region is irradiated by high-energy particles (e.g., electrons, high-energy photons, and the like). In another example, radiotherapy is provided using a heavy charged particle accelerator (e.g., protons, carbon ions, and the like).

The placement and dose of the radiation beam is accurately controlled to provide a prescribed dose of radiation to the targeted region (e.g. the tumour) and to reduce damage to surrounding healthy tissue (known as organs at risk or OARs). A "tumour" may refer to a cancerous tumour, a "target" may refer to a cancerous target, and a "target region" may refer to a region including a cancerous target.

An aspect of treatment planning concerns determining suitable characteristics of radiation to be delivered to produce a safe and effective dose. Characteristics of radiation relate to, for example, a fluence pattern. The fluence pattern may be dependent on beam arrangements, energies, and field sizes, which are in turn related to controllable parameters (which are optimisable). By determining suitable values for those parameters, a suitable fluence pattern may be obtained. A treatment plan may be determined by a treatment planning system.

Generating a radiation therapy treatment plan (treatment planning) comprises using an optimisation procedure to determine a set of optimum parameters that would deliver a suitable dose. The optimisation procedure may be based on clinical and dosimetric objectives and constraints. Examples of clinical and dosimetric objectives and constraints include maximum, minimum, and mean doses to a tumour and critical organs. Clinical and dosimetric objectives and constraints may be referred to as treatment-planning objectives.

The treatment planning procedure may include using a three-dimensional image of the patient to identify a target region and to identify critical organs near the tumour. The target region, area to be treated (e.g., a planned target volume (PTV)), and Organs at Risk (OARs) may be identified using segmentation. After segmentation, a dose plan may be created for the patient indicating the desirable amount of radiation to be received by the PTV (e.g., target) and/or the OARs. The PTV may have an irregular volume.

In a practical example, multiple anatomical structures (i.e., PTV, targets, and/or OARs) may be present. For example, in a head and neck treatment, there may be over 20 anatomical structures. For each structure, compliance with various treatment-planning objectives is desired. Structures and their objectives may be assigned different priorities in order to achieve a clinically acceptable plan. Determining a treatment plan to meet the various objectives is time-consuming and complex.

There is a need for improved methods and systems for generating treatment plans.

BRIEF DESCRIPTION OF FIGURES

Systems and methods in accordance with non-limiting examples will now be described with reference to the accompanying figures in which.

DETAILED DESCRIPTION

Figure 1A:
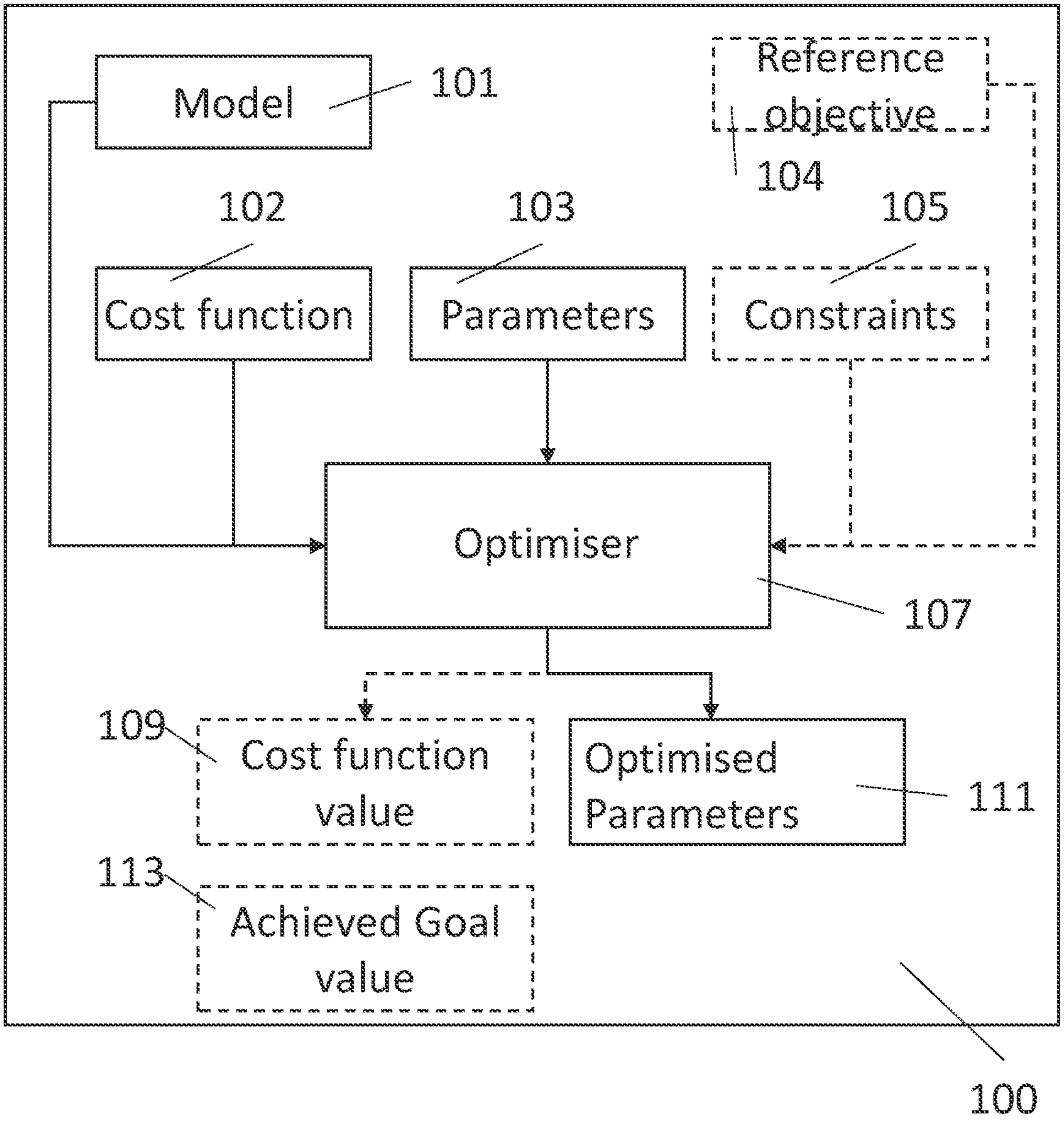
FIG. 1A shows a block diagram of an optimisation procedure according to an example.

As described above, the generation of a treatment plan may be time consuming and complex, particularly when many treatment-planning objectives are present.

Treatment planning comprises performing an optimisation procedure to optimise a number of parameters, the purpose being to provide a sufficiently high dose to the PTV while reducing the dose to the surrounding healthy tissue. By balancing the different treatment-planning objectives, for example by prioritising treatment-planning objectives that relate to the dose coverage at the PTV and then treatment planning objectives that relate to sparing OARs, a clinically suitable plan may be obtained. By prioritising one objective over another objective, it is meant that an optimisation procedure is performed based on a first objective, and then a further optimisation procedure is performed based on a second objective having lower priority than the first objective. It is understood that throughout this disclosure the terms optimise and optimize, and their variations, may be used interchangeably.

A user (e.g., a treatment planner, dosimetrist, clinician or health care worker) may achieve a clinically suitable plan as follows. For each treatment-planning objective, the user may configure the optimiser by defining e.g., a reference dose, reference volume, and/or cost function. An example of a treatment-planning objective may be stated as '97% of the volume of the PTV should receive at least 40 Gy'. The objective represents a goal to be achieved. The optimiser would then try to find optimised parameters that meet this goal. The solution found by the optimiser may or may not meet the desired goal (based on the anatomy, limitations of the radiotherapy machine and/or difficulty of the problem). Based on the achieved goal, optimisation may be repeated using a revised goal to be achieved. This approach is time consuming and leads to variable results, based on the user's choice of revised goal to be achieved. Furthermore, when a plurality of treatment-planning objectives is considered, this approach is repeated for each objective, making plan generation even more time consuming.

Some treatment-planning objectives are concerned with the dose to be delivered to a volume of an anatomical structure. Such treatment-planning objectives may be defined in terms of a dose value (reference dose) and a volume value (reference volume). The reference dose and reference volume are singular values. They do not correspond to the spatial dose distribution over the entire volume. Optimisation of treatment-planning objectives may use those singular reference dose and reference volume (rather than the dose distribution). The optimisation may not yield the desired result, particularly when multiple treatment planning objectives are present.

The methods and systems herein address a technical problem arising in the field of radiotherapy treatment planning, namely, how to improve generation of a treatment plan. In particular, the methods and systems are concerned with improving the outcome of the optimisation procedure (and thus, the suitability of the optimised parameters in the generation of a treatment plan) when a treatment-planning objective is concerned with the dose to be delivered to a volume of an anatomical structure.

This is achieved by performing optimisation according to a first treatment planning objective (first reference objective) to determine a dose-volume metric for the anatomical structure. The dose-volume metric is then taken into account in a subsequent optimisation based on another treatment planning objective (second reference objective). In particular, the dose-volume metric is used as a constraint in the subsequent optimisation. By using the above as a constraint, the outcome of the optimisation procedure may be improved.

The dose-volume metric comprises a dose value and a corresponding volume value. The dose-volume metric may be obtained from the dose distribution in the anatomical structure. The dose-volume metric is related to how much of the anatomical structure receives a given dose and/or what dose would be received by a given volume of the anatomical structure. An example of a dose-volume metric is “52 Gy at 85% volume”. For example, the dose-volume metric may be (i) what dose would be received by a prescribed volume of an anatomical structure (achieved dose at the reference volume), and/or (ii) what volume of an anatomical structure would receive a prescribed dose (achieved volume at the reference dose).

According to a first aspect, there is provided a method of radiation treatment planning for a radiotherapy system, the method comprising:

- receiving a first reference objective and a second reference objective, each reference objective representing a goal to be achieved by the radiotherapy system, and the first reference objective comprising a reference dose to be delivered to a reference volume of an anatomical structure,
- optimising a set of parameters, according to the received first reference objective and the received second reference objective, the set of parameters relating to characteristics of radiation to be delivered by the radiotherapy system, wherein optimising the set of parameters comprises:
  - optimising the set of parameters based on the first reference objective to obtain a dose-volume metric for the anatomical structure, and
  - further optimising the set of parameters based on the second reference objective using the dose-volume metric as constraint, and
- generating a radiation treatment plan using the further optimised set of parameters.

The generated radiation treatment plan is useable by the radiotherapy system for delivery of radiation therapy. The generated treatment plan may be outputted for delivery of radiation by a radiotherapy system.

In an example, the dose-volume metric comprises a dose at a corresponding volume of the anatomical structure. In an embodiment, the dose-volume metric comprises an achieved dose at a volume that is between 70% to 100% of the reference volume, and/or an achieved volume at a dose that is between 80% to 120% of the reference dose.

In an embodiment, the dose-volume metric comprises an achieved dose at the reference volume, and/or an achieved volume at the reference dose.

In some embodiments, optimising the set of parameters comprises: responsive to the dose-volume metric not meeting the first reference objective, further optimising the set of parameters based on the second reference objective using the dose-volume metric as constraint.

The dose-volume metric (e.g., achieved dose at the reference volume and/or the achieved volume at the reference dose) may not meet the first reference objective (comprising a reference dose at a reference volume) for several reasons. For example, the first reference objective might have been too strict and/or other pre-existing constraints might have restricted the solution space such that a set of parameters that would meet this objective could not be found.

In some embodiments, optimising the set of parameters comprises: responsive to the achieved dose at the reference volume or the achieved volume at the reference dose not meeting the first reference objective, modifying the achieved dose at the reference volume to obtain a relaxed dose, and further optimising the set of parameters based on the second reference objective using the relaxed dose at the reference volume and the achieved volume at the reference dose as constraints.

The relaxed dose is a dose value that is less restrictive than the achieved dose. Using the relaxed dose, instead of the achieved dose, provides ‘more room’ to the optimiser for subsequent optimisation steps.

In some embodiments, obtaining the dose-volume metric from the optimised set of parameters comprises: obtaining a dose distribution in the anatomical structure using the optimised set of parameters, and obtaining the dose-volume metric from the dose distribution. For example, the dose-volume metric is a dose X Gy that would be received by Y % of the anatomical structure.

In some embodiments, the dose distribution is represented by a dose-volume histogram, DVH.

In some embodiments, the first reference objective comprises any one of the following cost functions: a target penalty cost function; an underdose DVH cost function, an overdose DVH cost function, and a parallel cost function.

According to some examples, the second reference comprises a cost function that is the same as the first reference objective. For example, when the first reference objective comprises a target penalty cost function, and the second reference objective comprises a second target penalty cost function. Alternatively, the second reference comprises a cost function that is different from the first reference objective.

In some embodiments, optimising the set of parameters comprises:

- optimising the set of parameters based on the first reference objective, to obtain the dose-volume metric, and further optimising the set of parameters, using the dose-volume metric as objective, to obtain an intermediate set of parameters, further optimising the intermediate set of parameters, based on the second reference objective and using the dose-volume metric as constraint, to obtain the further optimised set of parameters.

In some embodiments, wherein the dose-volume metric comprises an achieved volume at the reference dose and/or an achieved dose at the reference volume, and wherein further optimising the set of parameters, using the dose-volume metric as objective, comprises using a weighted sum of a first cost function based on the achieved volume at the reference dose and a second cost function based on the achieved dose at the reference volume.

Performing a further optimisation, using the dose-volume metric as objective, further improves the outcome of the optimisation procedure.

According to another aspect, there is provided a method of radiation treatment planning for a radiotherapy system, the method comprising:

receiving a reference objective, the reference objective representing a goal to be achieved by the radiotherapy system, and the reference objective comprising a reference dose to be delivered to a reference volume of an anatomical structure, optimising a set of parameters, according to the received reference objective, the set of parameters relating to characteristics of radiation to be delivered by the radiotherapy system, wherein optimising the set of parameters comprises:

optimising the set of parameters based on the reference objective to obtain a dose-volume metric, and further optimising the set of parameters, based on the received reference objective and a further objective, the further objective being based on the dose-volume metric, generating a radiation treatment plan using the further optimised set of parameters.

The dose-volume metric (which may be an achieved dose at the reference volume, and/or achieved volume at the reference dose, for example) obtained after optimisation is taken into account in a further optimisation. In particular, the dose-volume metric is used as a further objective in the further optimisation, together with the received reference objective. By using the further objective, the outcome of the optimisation may be improved.

In some examples, further optimising the set of parameters, based on the received reference objective, and using a further objective that is based on the dose-volume metric, comprises using a weighted sum of a cost function of the received reference objective and a cost function based on the dose-volume metric.

According to another aspect, there is provided a treatment planning system comprising a processor configured to:

receive a first reference objective and a second reference objective, each reference objective representing a goal to be achieved by the radiotherapy system, and the first reference objective comprising a reference dose to be delivered to a reference volume of an anatomical structure, optimise a set of parameters, according to the received first reference objective and the received second reference objective, the set of parameters relating to characteristics of radiation to be delivered by the radiotherapy system, wherein optimising the set of parameters comprises:

optimising the set of parameters based on the first reference objective to obtain a dose-volume metric, and further optimising the set of parameters based on the second reference objective using the dose-volume metric as constraint, and generate a radiation treatment plan using the further optimised set of parameters.

According to another aspect, there is provided a radiation treatment planning system comprising a processor configured to:

receive a reference objective, the reference objective representing a goal to be achieved by the radiotherapy system, the reference objective comprising a reference dose to be delivered to a reference volume of an anatomical structure, optimise a set of parameters, according to the received reference objective, the set of parameters relating to characteristics of radiation to be delivered by the radiotherapy system, wherein optimising the set of parameters comprises:

optimising the set of parameters based on the reference objective to obtain a dose-volume metric, and further optimising the set of parameters, based on the received reference objective and a further objective that is based on the dose-volume metric, generate a radiation treatment plan using the further optimised set of parameters.

In embodiments, the treatment planning system comprises a processor configured to perform any of the methods above.

In embodiments, the methods are methods of radiation treatment planning for delivering radiation therapy by a radiotherapy system.

According to another aspect, there is provided a computer-readable medium comprising computer-executable instructions configured to cause a processor to perform any of the methods above.

The methods are computer-implemented methods. Since some methods in accordance with examples can be implemented by software, some examples encompass computer code provided to a general purpose computer on any suitable carrier medium. The carrier medium can comprise any storage medium such as a floppy disk, a CD ROM, a magnetic device or a programmable memory device, or any transient medium such as any signal e.g. an electrical, optical or microwave signal. The carrier medium may comprise a non-transitory computer readable storage medium.

FIG. 1A shows a block diagram of an optimisation procedure 100. The optimisation procedure 100 is applicable to the optimisation of a set of parameters (i.e. one or more parameters) for a radiotherapy system. The one or more parameters may be referred to as optimisable parameters, or as decision variables. Examples of optimisable parameters comprise parameters that relate to characteristics of radiation to be delivered by the radiotherapy system. For example, the set of parameters relates to a fluence map. The fluence map may also be referred to as an intensity profile. The fluence map may correspond to the weight of the beamlets (beamlets are described below). An example of a radiotherapy system will be described below.

The optimisation module 100 comprises an optimiser 107. Given a model 101 and one or more parameters 103, the purpose of the optimiser 107 is to provide a set of optimised parameters 111 that minimise a cost function 102. The optimizer comprises at least one optimization algorithm such as a simplex algorithm, a gradient-based algorithm, and an interior point algorithm, etc., and a combination thereof.

Other optimisation algorithms are also possible. An optimisation algorithm may be executed until a stopping criterion is reached. For example, a stopping condition may be any one or more of: a number of iterations being reached, a convergence criterion being met, and a constraint (such as constraint 105 described herein) being violated. A constraint may be a predefined constraint, defined in advance of the optimisation procedure being performed. Examples of predefined constraints are the clinical and planning constraints shown in rows a to I of Table 1. Alternatively, a constraint may be obtained from a previous optimisation procedure. Examples of optimization are provided in Monaco® Training Guide, Document ID: LTGMON0530 (Elekta AB). The optimisation procedure may, for example, correspond to the optimisation procedure described in European patent application publication EP3681600A1.

The model 101 is a representation of the physical problem. For radiotherapy treatment planning, the model 101 includes, for example, a dose distribution over voxels in a region. The dose distribution may be the dose at unit fluence. The region may correspond to an anatomical structure. The anatomical structure may comprise one or more of: a target, a region of healthy tissue (known as organs at risk or OARs), planned target volume (PTV), critical structures, or shell structures. These structures are determined and/or defined during a process known as segmentation. Shell structures are structures generated to tune the dose delivered to the tissue surrounding the target, and they may be used to control dose conformality. The dose distribution may be determined by pencil beam algorithms, convolution based algorithms and/or Monte Carlo (MC) based algorithms. Further details of how the dose may be determined are provided in Monaco® Training Guide, Document ID: LTGMON0530 (Elekta AB).

The one or more parameters 103 are optimizable parameters (also referred to as decision variables) for which the optimiser 107 attempts to find optimum values. The one or more parameters 103 may be initialised to a predetermined value. In an example, for IMRT and when the parameters 103 are the weight of beamlets, the parameters 103 may be initialised to a predetermined weight. Alternatively, the parameters 103 may be initialised to values determined in a previous step. For example, when a further optimisation is performed, the parameters may be initialised to values determined in a previous optimisation.

A beam may be divided into beamlets where the weight of each beamlet may be adjusted. A beam may be understood as a matrix of beamlets. Thus, a beam may be represented by a plurality of beamlets. The total dose distribution is then the weighted sum of the contribution of each beamlet at unit fluence (For example, the dose at a voxel k is given by $\Sigma X_n \cdot d_{n,k}$, where n is an index for beamlet n, $x_n$ is the weight of beamlet n, and $d_{n,k}$ is the dose at unit fluence at voxel k due to beamlet n). By tuning the weight of the beamlets, the radiation may be modulated. The weight of the beamlets may be adjusted by adjusting the configuration of a beam shaping apparatus, such as the part 850 of FIG. 8. For example, when the beam shaping apparatus is an MLC, the optimised beamlet weights (and hence the desired dose distribution) may be implemented by using different aperture shapes of the MLC (also referred to as segments) to shape the delivered radiation. The weight of a beamlet is related to the dose rate. The dose rate refers to how much dose a linac or energy source may deliver per unit time. For a fixed dose rate, the beamlet weight is proportional to the amount of time the beamlet is active. For example, a higher weight means the beamlet is kept active for a longer time. Thus, the weight of a beamlet is a function of dose rate and/or the duration for which the beamlet is kept active.

The cost function 102 is a mathematical formulation that relates the parameters 103 and the model 101. The cost function may be referred to as an objective function. The cost function 102 relates the dose distribution in the model 101 to a single value (the cost function value 109). For example, when the reference objective is "the mean dose for the bladder is less than 30 Gy", the cost function mathematically formulates and computes the mean dose for the bladder as a function of parameters 103, and compares the achieved mean dose to the reference of 30 Gy. During optimisation, the optimiser 107 seeks parameters that would minimize the difference between the achieved mean dose and the reference mean dose. The cost function value quantifies how close the dose in the model is to a desired value.

The cost function value 109 is value of the cost function when evaluated with the set of optimised parameters. The cost function value 109 is calculated by the optimiser during optimisation. The cost function value 109 may be referred to as a penalty. Optionally, the cost function value 109 is output by the optimiser.

The cost function value 109 defines a penalty for violating an objective or constraint. The penalty is evaluated by the optimiser during optimisation. Optionally, in constrained optimisation, only objectives contribute to the cost function.

The constraint 105 comprise one or more conditions that the optimised parameters 111 must satisfy. The constraint may be hard a constraint (which set conditions that the parameters are required to satisfy) or soft constraint (which have some variable values that are penalised in the cost function if some conditions are not satisfied). Constraints restrict the set of solutions that are obtainable. Constraints are used to define what is physically or clinically acceptable rather than what is mathematically possible. For example, for IMRT, a constraint may be that the weights of the beamlets must be non-negative (since a negative beamlet weight is not possible). Note that the constraint 105 is an optional feature. Additionally and optionally, the constraint 105 comprises an indication of a one or more cost function(s) 102 to be used. Yet optionally, the constraint comprises an indication of an anatomical structure to which the constraint is applicable. When a constraint 105 is used with a cost function 102, the constraint is met when the cost function value differs from the cost function evaluated at the constrained values by less than a predetermined amount.

The reference objective 104 represents a goal to be achieved. In an example, for IMRT, the reference objective comprises a dose-based objective and/or a volume-based objective. A dose objective may be defined in terms of a dose value (in Gy). An example of a dose objective may be stated as "the average dose to an OAR should be less than or equal to 30 Gy". A volume-based objective may comprise a relative volume or an absolute volume. The relative volume represents a fraction of a volume. For example, the relative volume is a percentage. The absolute volume may be defined in terms of physical dimensions (e.g., in mm, cm, $mm^3$, $cm^3$, etc.,). An example of a volume-based objective may be stated as "at least 90% of the volume of a PTV should receive a prescribed dose". In another example, a reference objective 104 may be stated as "at least X % of a first region receives at least Y Gy". The optimiser 107 may then determine optimised parameters 111 that result in an achieved goal value 113 that is close to the reference objective 104. The reference objective may be referred to as a treatment-planning objective. Note that the reference objective 104 is an optional feature. Additionally and optionally, the reference objective 104 comprises an indication of one or more cost function(s) 102 to be used. Yet optionally, the reference objective comprises an indication of an anatomical structure to which the goal to be achieved is applicable.

The reference objective is an anatomy specific function that establishes the dose and/or biological response goal. Constraints 105 are anatomy-specific functions that must be met. They may be referred to as hard constraints. When constraints are used together with objectives, constraints are always met, while objectives may not be met (instead, they are goals that the optimiser tries to achieve).

The cost function 102, together with the model 101, the parameters 103, constraints 105 (optional) and reference objective 104 (optional), define the problem to be solved.

The cost function 102, constraints 105, reference objective 104, either alone or in any combination, may be referred to as a treatment-planning objective. The treatment-planning objective may be associated to an anatomical structure. In other words, a treatment-planning objective may comprise any of cost function 102, constraint 105, reference objective 104. An example of a treatment-planning objective may be stated as "97% of the volume of a PTV should receive a dose of at least 30 Gy, using a "Target Penalty" cost function". Other examples of treatment planning objectives are listed in row m to x in Table 1 below.

The optimiser 107 aims to find a set of optimised parameters 111 for which the cost function 102 is minimised. The optimised parameters 111 are an output of the optimiser 107. In an example, when a reference objective 104 is present, the optimiser 107 minimises the difference between the goal value 113 and a reference objective 104.

Optionally, the optimiser 107 outputs the cost function value 109. The cost function value 109 is the value of the cost function 102, when evaluated with the optimised parameters 111.

Optionally, the optimiser 107 outputs an achieved goal value 113. The achieved goal value 113 is comparable to the reference objective. An achieved goal value 113 represents a value that has the same units as a given reference objective. The achieved value 113 may be different from the cost function value 109. Unlike the cost function value 109, which may be a number that is an evaluation of the cost function, the achieved value 113 may have a physical meaning. In an example, when the reference objective comprises a dosimetric objective in Gray (Gy), the achieved goal value also relates to a dose (i.e. it has the units of Gy and/or the same physical meaning as the reference objective). In an example, when the reference objective comprises a reference volume and a dose value, the achieved goal value also relates to a reference volume and a dose value (i.e. it has the same physical meaning as the reference objective). As will be described below in relation to Table 1, a reference objective might be DVH-based and may be for a percentage of a volume to receive a predetermined dose. The cost function value 109 may be a number that corresponds to a cost function evaluated with a set of optimised parameters. The achieved goal value 113 would be the achieved percentage of the volume that receives the predetermined dose. In other words, achieved goal value 113 is comparable to the reference objective.

Figure 1B:
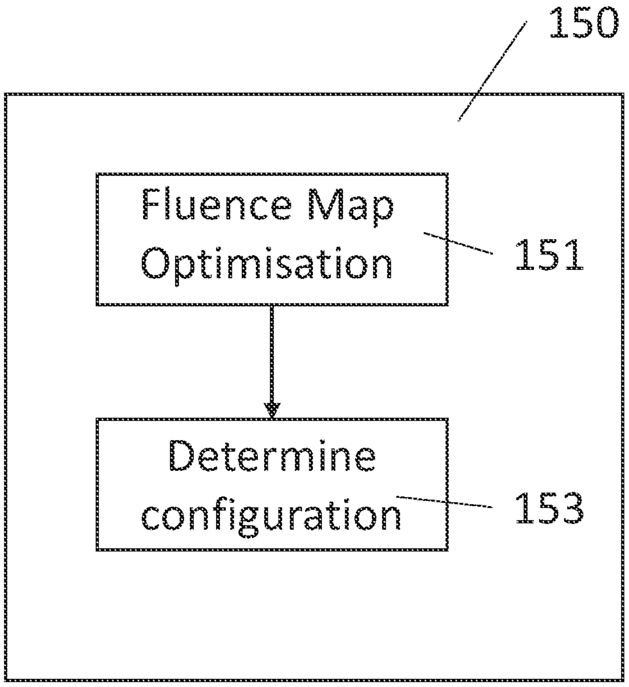
FIG. 1B shows a block diagram of an optimisation procedure applied to IMRT according to an example.

FIG. 1B shows an example of a two-stage optimisation procedure 150 for IMRT. The optimisation procedure may also be applied to volumetric modulated arc therapy (VMAT). Although this example applies to IMRT, it is noted that optimisation procedure 100 may be applied to other modes of radiotherapy.

In IMRT, one or more radiation beams are directed to a tumour. The intensity of each beam profile is non-uniform. The aim of optimisation procedure 150 is to modify the intensity profile such that a high enough dose is delivered to the tumour, while reducing the dose delivered to healthy organs.

The method of optimisation for IMRT 150 comprises two stages. The first stage 151 is fluence map optimisation (FMO) and the second stage 153 is the determination of a configuration of the radiotherapy system. In FMO (stage 151), an optimal fluence map is determined. The optimal fluence map is then used to determine a configuration for the radiotherapy system in stage 2. FMO step 151 will be described next. Step 153 will be described further below.

For fluence optimisation, each beam is divided into a number of beamlets. The contribution of each beamlet, at unit fluence, to voxels is then calculated. Initially, the beamlets may be equally weighted and may contribute equally to the dose distribution. During optimisation, the weight of each beamlet is adjusted such that a cost function is minimised. By multiplying the weight with the contribution of each beamlet at unit fluence, and then summing for all beamlets, the full dose distribution may be obtained. The full dose distribution may be compared with any constraints and/or reference objective to determine if the optimised solution is suitable.

The optimisation procedure for FMO may also be expressed as follows. The optimisation procedure for FMO may be performed by the optimisation procedure 100 described herein.

Optimisation comprises minimizing a cost function f(x) by determining suitable values of parameters x based on certain constraints g. For FMO, the parameters x correspond to the weight of the beamlets (x may also be referred to as decision variables, which are the parameters that may be controlled). The output of FMO (Stage 151) comprises parameters x.

The constraints g comprise restrictions. An example of a restriction is a minimum dose at voxels corresponding to a target, or a maximum dose at voxels corresponding to OAR, etc., In an example, a cost function f(x) is:

$$f(x) = T1 + T2 + \ldots + T3$$

where e.g. T1=>$x_n$. $d_n$, where, when x corresponds to weight of a beamlet, $d_n$ represents the dose that each beamlet gives to a voxel at unit intensity. $d_n$ is a non-optimizable parameter (e.g., it may depend on machine configuration and/or properties of the tissue). $d_n$ may be obtained from model 101 described above. For example, from the model 101, it is known whether a voxel n belongs to a target, an OAR, etc., In an example, the dose $d_n$ may be determined by pencil beam algorithms, convolution based algorithms and/or Monte Carlo (MC) based algorithms. Optionally, dose calculations use pencil beam algorithms or convolution based algorithms (which are fast but have reduced accuracy). Further details of how the dose $d_n$ may be determined are provided in Monaco® Training Guide, Document ID: LTG-MON0530 (Elekta AB).

The output of stage 1 may include a dose distribution.

In this example, the objective function f(x) is the sum of the total dose (T1, T2 . . . . T3) where each of T1, T2 . . . . T3 represent the dose on different structures. Note that alternative formulations of the problem to be solved (e.g. by defining different cost functions or constraints) may be used.

In an example, the requirement for the dose at a target to be above a certain amount may be formulated as a constraint. Alternatively, such a requirement could be formulated as a reference objective.

Step 151 provides a set of optimised parameters (e.g., beamlet weights x) that would provide an optimum intensity map (or fluence map). To be ready for delivery by the radiotherapy system, a further step (step 153) is required to translate each optimised beamlet weight into a configuration of the machine that would deliver the optimum fluence.

Determining a configuration (step 153) is described next.

At step 153, the output from step 151 is turned into a configuration of a radiotherapy system. The configuration is useable by a radiotherapy apparatus (examples of which are described herein) for delivering radiation therapy. For example, the configuration of the radiotherapy system comprises a set of (i.e., one or more) aperture configurations. The shapes and weights of the aperture configurations are selected to meet the same goal as in the first stage. Here, shape refers to a shape of an opening. Each shape may be referred to as a segment. Here, weight refers to the weight of each segment. The weight of a segment is related to the dose rate. For a fixed dose rate, the segment weight is proportional to the amount of time the beam is delivered through the segment. For example, a higher segment weight means a longer delivery time through the segment. Thus, the weight of a segment is a function of dose rate and/or the duration for which the beam is delivered through the segment. Aperture configurations may be realised by a beam shaping apparatus, such as part 850 of FIG. 8. When the beam shaping apparatus is an MLC, the shapes are defined by leaf positions.

An aperture configuration may be referred to as a control point or a segment. The control point and/or segment comprise radiation information (e.g. energy, dose) and geometric information such as gantry angle and leaf position.

The shapes and weights of the apertures may be determined by applying algebraic and trigonometric considerations to the arrangement of the aperture in order to implement the optimised beamlet weights of step 151.

Alternatively, step 153 comprises performing a second stage optimisation procedure to determine an optimised aperture configuration that would implement the optimised fluence pattern determined in step 151. The second stage optimisation procedure may be referred to as aperture optimisation, or aperture refinement.

Aperture optimisation may comprise the following:

- Receiving a set of beamlet weights (e.g., from step 151)
- Performing optimisation to determine optimised aperture shapes and, optionally, weights. The optimisation may be performed using an optimisation procedure such as in FIG. 1B, for example. Other optimisation procedures are possible.

When the beam shaping apparatus comprises an MLC, aperture optimisation may comprise:

- Receiving a set of beamlet weights from FMO and/or fluence profiles (e.g., from step 151)
- Converting the received profile into beamlet widths (the opening between a leaf pair). This results in a segment.
- Optimising the weights of the resulting segments.
- Optionally, optimising shapes of the resulting segments (using a procedure referred to as segment shape optimisation).

Note that the optimisation steps in step 153 may comprise a calculation of the dose distribution. The dose distribution may be calculated using pencil beam algorithms, convolution-based algorithms and/or Monte Carlo (MC) based algorithms. Optionally, dose calculations in step 153 use MC based algorithms (which are more accurate but computationally expensive).

Further details of aperture optimisation are provided in Monaco? Training Guide, Document ID: LTGMON0530 (Elekta AB).

Note that the procedure of FIG. 1B relates to one specific angle. In an approach, a prior step would be to determine the angles from which radiation is to be delivered from. The beam angle optimisation (BAO) procedure is carried out before the procedure of FIG. 1B. The procedure of FIG. 1B is then carried out for each determined angle.

While the example of FIG. 1B relates a two-stage optimisation procedure (FMO at step 151 and determination of a configuration at step 153) for IMRT, it is noted that alternative methods of optimisation, such as Direct Machine Parameter Optimisation (DMPO), may be used instead. In DMPO, the decision variable x corresponds to a parameter of a machine (e.g. an MLC leaf position) that delivers radiation. Yet alternatively, the decision variable x may correspond to any one or more of the following: number of beams, beam angles, a dose per beam, beamlet weights, segment or control point shapes, segment or control point weights, dose-volume histogram information, a dose excess value.

Returning to cost function 102 in optimisation procedure 100, examples of cost functions comprise: Target EUD, Target Penalty, Quadratic Overdose, Quadratic Underdose, Serial, Parallel, Maximum Dose, Overdose DVH, Underdose DVH. The cost functions are briefly defined below. Each cost function offers different calculation methods.

When the cost function comprises any of target penalty, parallel, overdose DVH, and Underdose DVH, the reference objective is a dose value and a relative volume component (e.g. a percentage) or an absolute volume (e.g. in cc).

When the cost function comprises any of Target EUD, quadratic overdose, serial, maximum dose, or conformality, the reference objective is a dose value.

Cost functions such as serial, parallel, quadratic overdose, overdose DVH, or maximum dose aim to limit the dose at an anatomical structure. For example, for these cost functions, a penalty is increased as the achieved dose exceeds a reference dose. The penalty increases the further the achieved dose is above the reference dose.

Cost functions such as quadratic underdose or underdose DVH aim to increase the dose at an anatomical structure. Cost functions such as Target EUD and Target Penalty aim to increase the dose at a structure. For example, these cost functions are used for target or PTV and a penalty increases when the achieved dose is lower than a reference dose. The penalty increases the further the achieved dose is below the reference dose.

Some of the above cost functions also take a unitless number as input. The unitless number is a power law exponent.

The Target EUD cost function defines a structure as a target volume and expresses the probability that a target cell survives a given dose. This cost function requires a prescribed dose as input (i.e. the reference objective for this cost function is a dose value). The prescribed dose, in Gy, is an equivalent uniform dose (EUD). An EUD is a homogenous dose that, if delivered at an anatomical structure, has the same clinical effect that a non-homogenous dose distribution would.

The Target Penalty cost function takes as input a prescribed dose. A minimum volume is also provided as input (i.e., the reference objective for this cost function is a dose and a relative volume). The Target Penalty is a quadratic penalty which starts at a threshold dose. It produces steeper dose gradients after a target threshold is met. The Target Penalty is used to define the requirement that at least some fraction of the total anatomical structure volume should receive at least the target dose. For example, the target penalty is defined as:

$$\text{Target Penalty}(D; V, \Delta) = \frac{1}{|V|}\sum_{i\in V}|V_i|[D_i - \Delta]_-^2$$

where V is the total volume of the associated anatomical structure, $V_i$ is the volume occupancy of voxel i, Δ is the prescribed dose (reference dose), $D_i$ is the dose at voxel i. The $[.]_-^2$ operator means one-side penalty (i.e. the cost function value is only considered when the voxel dose is <the reference dose. For example, if the threshold dose (reference dose) is 70 Gy, and if a voxel dose is 75 Gy, then the term "$[.]^2_-$" is zero (since the voxel dose is above the reference dose), but if a voxel dose is 65 Gy, then this term "[.]2–" . . . is (65-70)/\2=25.

Note that although the mathematical expression for the Target Penalty cost function shown in the above example does not include a reference volume, the reference volume is provided by the user. The volume that receives the prescribed dose A is determined from the dose distribution.

For example, when the target penalty being used as an objective (and the goal of the optimiser being to minimize the cost function value, with a reference dose of 70 Gy, the optimizer will try to push all voxel doses higher than 70 Gy. If it turns out all voxel doses are indeed higher than 70 Gy, then the final cost function value is 0, and the volume is 100% (because all voxel doses exceed the threshold dose 70 Gy). If only 80% of voxel doses exceeds the threshold dose, then the volume is 80%. When the target penalty cost function is used as an objective, a weighting factor that is dependent on the reference volume may be assigned to the cost function. For example, if the reference volume is 90%, then the internal weighting factor is "a"; and if the reference volume is 100%, then the internal weighting factor is "b", where "b" is much larger than "a". This is to let optimizer 'work harder' if the reference volume is 100%. The quadratic overdose (QO) cost function is a cost function used to limit the dose in the structure to which it is applied. The QO may be applied to either targets or OARs. The QO cost function may be used to limit hot spots in a target. The QO cost function takes as input a maximum dose and a root-mean square (RMS) dose excess (i.e. the reference objectives comprises two dose values). The maximum dose defines a dose beyond which a penalty is incurred. The RMS dose excess defines the amount of violation that is acceptable.

The quadratic underdose cost function is a cost function that is applied to a target volume. The quadratic underdose function implements a quadratic penalty. The cost function takes as input a minimum dose in Gy and a dose deficit in Gy (i.e., the reference objective comprises two dose values). The minimum dose is the minimum dose allowable in a target and represents the dose under which a penalty is incurred. The dose deficit is analogous to the RMS dose excess in that it defines the amount of violation from the prescription that is acceptable.

The Serial cost function is generally used with serial OARs. Serial anatomical structures are those where high doses are harmful even if limited to small volumes. Examples include the spinal cord and bowel. This cost function applies large penalties for hot spots even if they are small in volume. The cost function takes as input an EUD in Gy and a power law exponent k (i.e., the reference objective comprises a dose value and a unitless number).

The Parallel cost function is generally used for parallel OARs. Parallel structures are those where very high doses in small volumes are tolerated, if the rest of the organ is spared. Examples are lungs, parotids, kidneys, liver. The cost function takes as input a reference dose in Gy, a mean organ damage (which is a fraction of the volume of the structure that can be sacrificed), and power law exponent p (i.e. the reference objective comprises a dose value, a relative volume, and a unitless number). The parallel cost function may be referred to as partial volume (PV) cost function. Note that the Parallel cost function may also be used on a target, to prevent a too high dose on the target.

For example, the parallel cost function may be defined as:

$$\text{Parallel}(D; V, \Delta, p, \zeta) = \frac{1}{|V|}\sum_{i\in V}\frac{|V_i|\left(\frac{D_i}{\Delta}\right)^p}{1+|V_i|\left(\frac{D_i}{\Delta}\right)^p} \le \zeta$$

where, ξ is the reference volume (%) (also referred to as a mean organ damage (%)), V is the total volume of the associated anatomical structure, $V_i$ is the volume occupancy of voxel i, Δ is the prescribed dose (reference dose), $D_i$ is the dose at voxel i.

The Maximum Dose cost function is effectively a hard barrier that can be applied to target structures or OAR. The Maximum Dose cost function has a penalty that takes effect whenever voxels cross a maximum dose threshold. The cost function takes as input maximum dose in Gy (i.e., the reference objective comprises a dose value)

The Overdose DVH cost function takes as input an objective dose in Gy and a maximum volume (i.e., the reference objective comprises a dose value and a relative volume). This cost function may be applied to OARs, and/or it may also be applied to a target (e.g., to prevent too much dose). The purpose is to keep the volume that receives more than the objective dose below the relative volume.

For example, the overdose DVH, ODVH, may be defined as:

$$ODVH(D; V, \Delta, d_0) \le \zeta$$

$$ODVH(b) = \begin{cases} \frac{0.5}{|V|}\sum_{i\in V}|V_i|b_i \times b_i & 0 < b_i \le 1 \\ \frac{1}{|V|}\sum_{i\in V}|V_i|\left(1 - \frac{0.5}{b_i \times b_i}\right) & b_i > 1 \\ 0 & \text{else} \end{cases}$$

$$b_i = \frac{D_i - \Delta + d_0}{d_0}$$

Where, ξ is the maximum volume (reference volume), V is the total volume of the associated anatomical structure, V; is the volume occupancy of voxel i, A is the prescribed dose (reference dose), $D_i$ is the dose at voxel I, and, for example, $d_0$=0.04Δ.

The Underdose DVH cost function takes as input an objective dose in Gy and a minimum volume (i.e., the reference objective comprises a dose value and a relative volume). This cost function is applied to targets. The purpose is to keep the volume of the target that receives less than the objective dose above the minimum volume.

For example, the underdose DVH, UDVH (b), may be defined as:

$$UDVH(D; V, \Delta, d_0) \leq (1-\zeta)$$

$$UDVH(b) = \begin{cases} \frac{0.5}{|V|}\sum_{i\in V}|V_i| b_i \times b_i & 0 < b_i \leq 1 \\ \frac{1}{|V|}\sum_{i\in V}|V_i|\left(1 - \frac{0.5}{b_i \times b_i}\right) & b_i > 1 \\ 0 & \text{else} \end{cases}$$

$$b_i = \frac{-D_i - \Delta + d_0}{d_0}$$

Where, ξ is the minimum volume (reference volume), V is the total volume of the associated anatomical structure, $V_i$ is the volume occupancy of voxel i, Δ is the prescribed dose (reference dose), $D_i$ is the dose at voxel I, and, in an example, $d_0=0.04\Delta$.

Further details of the cost functions are provided in Monaco® Training Guide, Document ID: LTGMON0530 (Elekta AB).

Figure 2:
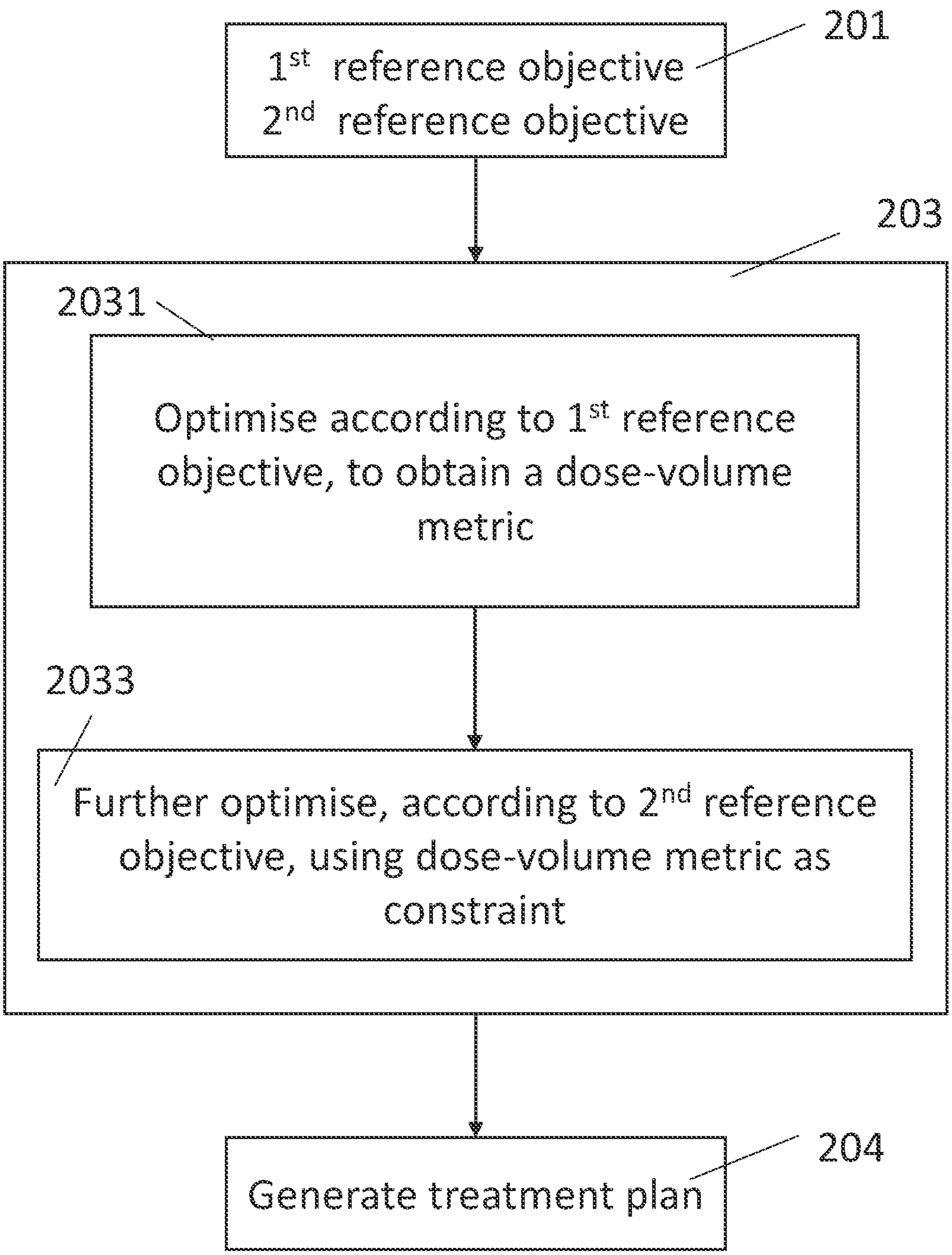
FIG. 2 shows a flow chart of a method of radiotherapy treatment planning according to an embodiment.

FIG. 2 shows a flow chart of a method of radiation treatment planning according to an embodiment. The method generates a treatment plan that is useable by a radiotherapy system (such as the radiotherapy system 600 of FIG. 6) for delivering radiation therapy. The method of FIG. 2 may be performed by the treatment planning system 610 described in relation to FIG. 6.

At step 201, a first reference objective and a second reference objective are received. Each reference objective represents a goal to be achieved when delivering radiation by a radiotherapy system. Optionally, the goal is a clinical goal prescribed by a user (e.g. physician). The reference objective corresponds to the reference objective 104 described herein.

The first reference objective comprises a reference dose to be delivered to a reference volume of an anatomical structure. The reference dose is a dose value and has units of e.g., Gy. The reference volume is a volumetric quantity and may be an absolute quantity that has units of e.g., mm, cm, $mm^3$, $cm^3$, cc etc., or a relative quantity that is defined as a fraction or a percentage of the volume of an anatomical structure. An example of a first reference objective is 60 Gy at 99.5% volume of a target.

For example, when the anatomical structure is a target, it is desired that the entire structure received the prescribed dose (reference dose). In other words, it is desired that 100% of the structure receives the prescribed dose. In practice, this may not be possible and a reference volume is provided to indicate an acceptable volume of the structure that should receive the prescribed dose (reference dose). The reference volume may be 90%, 95% or 99.5%, for example. When the when the anatomical structure is an OAR, it its desired that the OAR receives as little dose as possible. For example, it may desired that 90% of a structure receives less than a prescribed dose.

At step 203, optimisation is performed to optimise a set of parameters (i.e. one or more parameters). Optimisation is performed according to the first reference objective and the second reference objective received at step 201. The aim of optimisation is to seek values of parameters that would achieve the received reference objectives. Step 203 comprises steps 2031 and 2033. Optionally, at step 201 and/or 203, one or more cost functions to be used with each reference objective during optimisation is received. The cost function(s) may be provided by a user. For example, the cost function comprises any one or more of: a Target Penalty cost function; an Underdose DVH cost function, an Overdose DVH cost function, and a Parallel cost function.

At step 2031, the set of parameters is optimised according to the first reference objective, and a dose-volume metric is obtained. The dose-volume metric may be an achieved dose at the reference volume, and/or an achieved volume at the reference dose, for example. An example of a dose-volume metric is 50 Gy is received by 80% of the structure. The optimisation at step 2031 may be implemented by the optimisation procedure 100 described in FIG. 1A, for example.

In more detail, in the optimisation of step 2031, an optimisation algorithm is executed until a stopping condition is met. For example, a stopping condition may be any one or more of: a number of iterations being reached, a convergence criterion being met, and a constraint being violated. A constraint may be a predefined constraint, defined in advance of the optimisation procedure being performed. Examples of predefined constraints are the clinical and planning constraints shown in rows a to I of Table 1. Alternatively, a constraint may be obtained from a previous optimisation procedure. After the optimisation has stopped, a set of optimised parameters is obtained. An achieved goal value, a cost function value, and/or a dose distribution are also available. From the output of the optimisation procedure, a dose-volume metric may be obtained. For example, the dose-volume metric may be obtained from the dose distribution.

At step 2033, further optimisation is performed according to the second reference objective, and using the dose-volume metric as a constraint. The optimisation at step 2033 may be implemented by the optimisation procedure 100 described in FIG. 1A, for example. The optimisation of step 2033 is similar to that of step 2031, except that the optimiser seeks to meet the second reference objective, using a constraint derived from the dose volume-metric. For example, when the dose-volume metric obtained at step 2031 is '50 Gy is received by 80% of the structure', then at step 2033, the optimisation procedure is constrained to find parameters such that the condition of '50 Gy is received by 80% of the structure' is met. Additionally, and optionally, the constraint based on the dose-volume metric comprises the same cost function as for the first reference objective. The constraint may relate to the same anatomical structure as the first reference objective. Alternatively, the constraint is based on a cost function that is different from the first reference objective. Yet alternatively, the constraint relates to a different anatomical structure than the first reference objective.

Using the dose-volume metric from step 2031 as a constraint in step 2033 may be understood as automatically adding a constraint for step 2033. No user input is required.

In relation to step 203, when a dose-volume metric is obtained (at step 2031), then the dose-volume metric is used as a constraint in step 2033.

The outcome of step 2033 is a further optimised set of parameters. An achieved goal value, a cost function value, and/or a dose distribution will also be available.

At step 204, a treatment plan is generated using the further optimised set of parameters. The treatment plan of step 204 may be used for delivery of radiation therapy. The treatment plan comprises the further optimised set of parameters that relate to the characteristics of radiation to be delivered by a radiotherapy system. For example, step 204 may correspond to step 153 described in relation to FIG. 1B.

Additionally and optionally, the dose-volume metric may be the dose that would be received by the prescribed volume of the anatomical structure (the achieved dose at the reference volume) and/or the volume of the anatomical structure which would receive the reference dose (the achieved volume at the reference dose). In relation to step 203, when an achieved dose at the reference volume is obtained (at step 2031), then the achieved dose at the reference volume is used as a constraint in step 2033. Similarly, when an achieved volume at the reference dose is obtained (at step 2031), then the achieved volume at the reference dose is used as a constraint in step 2033. When both an achieved dose at the reference volume and an achieved volume at the reference dose are obtained in step 2031, any one or both may be used as a constraint in step 2033.

Additionally and optionally, the second reference objective comprises a reference dose to be delivered to a reference volume. Alternatively, the second reference objective may comprise a reference dose only. Yet optionally, the second reference objective may relate to the same anatomical structure as the first reference objective, or alternatively to a different anatomical structure.

Additionally and optionally, at step 2031, a dose distribution is obtained. The dose distribution is obtained using the optimised parameters from step 2031. From the dose distribution, the dose-volume metric may be derived. Optionally, from the dose distribution, a dose-volume histogram (DVH) may be derived. The dose distribution may be represented by a DVH. The dose-volume histogram, DVH, relates the radiation dose to the volume of an anatomical structure. The DVH is a 2D representation of the three-dimensional dose distribution. Optionally, the dose-volume metric is derived from the DVH.

Additionally and optionally, when step 2031 comprises deriving both the dose that would be delivered to the reference volume of the anatomy (the achieved dose at the reference volume) and the achieved volume at the reference dose, at step 2033, further optimisation is performed according to the second reference objective, using both the achieved dose at the reference volume and the achieved volume at the reference dose as constraints.

Additionally and optionally, when the dose-volume metric comprises an achieved volume at the reference dose, step 2033 is performed responsive to the achieved volume at the reference dose not meeting the first reference objective. By not meeting the reference objective, it is meant that the achieved volume at the reference dose deviates from the first reference objective by a predetermined amount. In particular, it is meant that either the achieved dose at the reference volume deviates from the reference dose by a predetermined amount, or the achieved volume deviates from the reference volume by a predetermined amount, or both. Yet optionally, in response to the achieved volume at the reference dose meeting the first reference objective, step 2033 comprises performing further optimisation according to the second reference objective; however, the achieved volume at the reference dose is not used as a constraint. The achieved dose at the reference volume is also not used as a constraint.

Additionally and optionally, in relation to step 2033, responsive to the achieved dose at the reference volume, or the achieved volume at the reference dose not meeting the first reference objective, the achieved dose at the reference volume is modified to obtain a relaxed dose, and the relaxed dose at the reference volume is used as a constraint in the further optimisation. Optionally, the achieved volume at the reference dose is used as a constraint, together with the relaxed dose at the reference volume. By modifying the achieved dose to obtain a relaxed dose, it is meant that the achieved dose is modified using a predetermined value (relaxation value). By modifying, it is meant, for example, that an operation comprising any of multiplication, division, addition or subtraction between the achieved dose and the relaxation value is performed to obtain a relaxed dose. The relaxed dose may be less strict than the achieved dose at the reference volume. For example, the relaxed dose may be further from the first reference objective than the achieved dose at the reference volume is from the first reference objective.

Additionally and optionally, the first reference objective comprises any one of the following cost functions: a target penalty cost function; an underdose DVH cost function, an overdose DVH cost function, and a parallel cost function. As described herein, a reference objective may comprise a cost function. For example, the first reference objective may be that at least a fraction of an anatomical structure achieves the prescribed dose, where any deviation from the prescribed dose is penalised according to the cost function. During optimisation, the cost function is minimised and hence the deviation of the achieved dose from the prescribed dose is also minimised. For example, a first reference objective could be that 99.5% of a PTV (reference volume) receives 60 Gy (the reference dose), and that a Target Penalty cost function is minimised during optimisation.

Additionally and optionally, constraints used in step 2033 comprise the same cost function as the first reference objective. A constraint may have an associated cost function. For example, when the first reference objective: to achieve a dose of 60 Gy in 99.5% of the volume of a target, using a Target Penalty cost function, the constraint may be that 99.5% of the volume of the anatomical structure receives 52 Gy using a Target Penalty cost function. A constraint is a condition that has to be met by the optimiser. The constraint is met when the Target Penalty cost function, evaluated with a dose at the reference volume, differs from the Target Penalty cost function evaluated at 52 Gy and 99.5% volume (reference volume) by less than a predetermined amount.

It is noted that the second reference objective may relate to the same or a different anatomical structure. The second reference objective has a lower priority than the first objective. The second reference objective may comprise the same or a different cost function. Further optimisation is carried out based on the second reference objective, using the achieved volume at the reference dose (that have been obtained during the previous optimisation based on the first reference objective) as a constraint.

Additionally and optionally, in relation to step 203, the optimisation procedure comprises optimising the set of parameters based on the first reference objective (which comprises a reference dose and at a reference volume of an anatomical structure) to obtain (i) an achieved dose at the reference volume, and/or (ii) an achieved volume at the reference dose. Further optimisation is then performed, using the (i) achieved dose at the reference volume and/or the (ii) achieved volume at the reference dose as objective(s), to obtain an intermediate set of parameters. The further optimisation may relate to the same anatomical structure as the initial optimisation. Further optimisation using (i) achieved dose at the reference volume and/or the (ii) achieved volume at the reference dose as objectives may provide an improved set of parameters (intermediate set of parameters), compared to the initial optimisation that was based on the reference dose at the reference volume. The intermediate set of parameters are further optimised, based on the second reference objective and using the (ii) achieved volume at the reference dose as constraints, to obtain the further optimised set of parameters. Note that each optimisation is performed until a stopping criterion is met, as described in relation to step 2031. Optionally, the further optimisation based on the (i) achieved dose at the reference volume and/or the (ii) achieved volume at the reference dose as objective(s), to obtain an intermediate set of parameters, is based on the same cost function as for the initial optimisation according to the reference objective.

Note that, optionally, when further optimising the set of parameters, using the achieved volume at the reference dose and the achieved dose at the reference volume as objectives, a cost function may comprise a weighted sum of a first cost function based on the achieved volume at the reference dose and a second cost function based on the achieved dose at the reference volume may be used. For example, the cost function, F, may be: $F(d_{ref}, V_{ret}, d_{ach}, V_{ach}, x)=w_1f_1(d_{ref}, V_{ach}, X)+w_2f_2(d_{ach}, V_{ref}, x)$, where x represents the optimizable parameters, $d_{ref}$ is the reference dose, $V_{ref}$ is the reference volume, $d_{ach}$ is the achieved dose at the reference volume, $V_{ach}$ is the volume that would receive the reference dose, $w_1$ is the weight assigned to the first cost function $f_1$, and $w_2$ is the weight assigned to the second cost function $f_2$. $w_1$ and $w_2$ may be equal or different.

Example scenario—An example of a scenario according to FIG. 2 is described next. In an example, the first reference objective is to achieve a dose of 60 Gy in 99.5% of the volume of a target. After optimisation according to the first reference objective (step 2031), it is determined that a dose of 52 Gy is achieved in 99.5% of the volume (achieved dose at the reference volume). It is also found that 80% of the volume of the target would receive the reference dose of 60 Gy (achieved volume at reference dose). Further optimisation (step 2033) is then performed according to a second reference objective, using the 60 Gy in 80% of the target volume (achieved volume at reference dose) as a constraint. A further optimised set of parameters is obtained, and a treatment plan is generated from those parameters. The further optimisation (step 2033) may use the dose of 52 Gy in 99.5% of the volume (achieved dose in reference volume) as an alternative to the achieved volume at reference dose or as an additional constraint.

Figure 3:
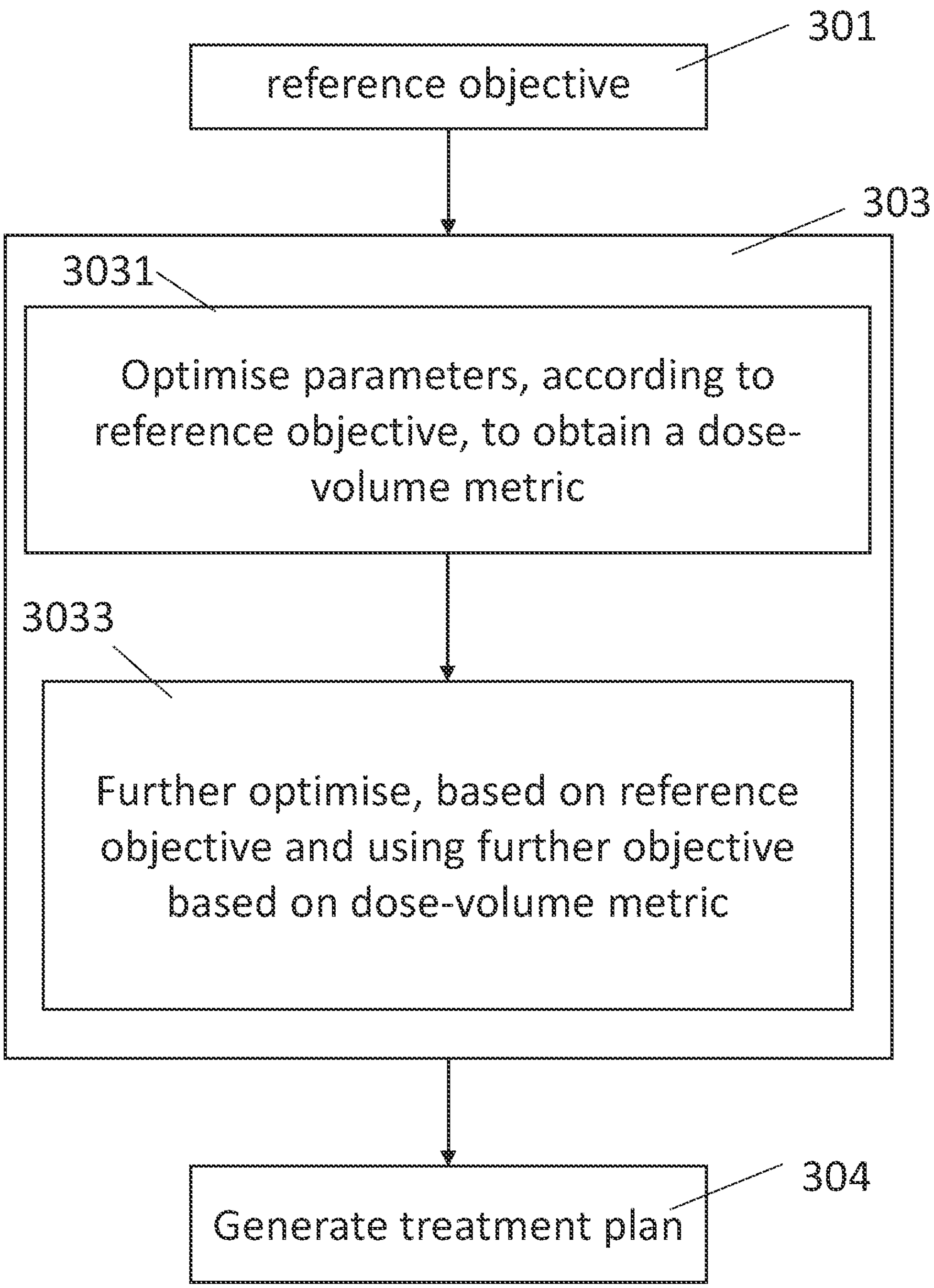
FIG. 3 shows a flow chart of a method of radiotherapy treatment planning according to an embodiment.

Note that the second reference objective may relate to the same or a different anatomical structure. The second reference objective may relate to a different treatment-planning objective altogether. FIG. 3 shows a flow chart of a method of radiation treatment planning according to an embodiment. The method generates a treatment plan that is useable by a radiotherapy system (such as the radiotherapy system 600 of FIG. 6) for delivering radiation therapy. The method of FIG. 3 may be performed by the treatment planning system 610 described in relation to FIG. 6.

At step 301, a reference objective is received. The reference objective represents a goal to be achieved when delivering radiation by a radiotherapy system. Optionally, the goal is a clinical goal prescribed by a user (e.g., physician). The reference objective corresponds to the reference objective 104 described herein. The reference objective corresponds to the first reference objective described in relation to FIG. 2.

At step 303, optimisation is performed to optimise a set of parameters (i.e. one or more parameters). Optimisation is performed according to the reference objective received at step 301. The aim of optimisation is to seek values of parameters that would achieve the received reference objective. Step 303 comprises steps 3031 and 3033. Optionally, at step 301 and/or 303, a cost function to be used with the reference objective during optimisation is received. The cost function may be provided by a user.

Step 3031 is analogous to step 2031 except that the reference objective is used instead of the first reference objective. An outcome of step 3031 is a dose-volume metric.

At step 3033, further optimisation is performed, based on the reference objective and using a further objective based on the dose-volume metric. Further optimisation using the further objective may provide an improved set of parameters (further optimised set of parameters), compared to the initial optimisation that was based only on the reference objective. Note that each optimisation is performed until a stopping criterion is met, as described in relation to step 2031.

At step 304, a treatment plan is generated using the further optimised set of parameters from step 303. Step 304 corresponds to step 204 of FIG. 2.

Additionally and optionally, the dose-volume metric may be the dose that would be received by the prescribed volume of the anatomical structure (the achieved dose at the reference volume) and/or the volume of the anatomical structure which would receive the reference dose (the achieved volume at the reference dose).

Additionally and optionally, the further optimisation of step 3033 uses a cost function comprising a weighted sum of the reference objective and the further objective. For example, the cost function, F, may be: $F(d_{ref}, V_{ref}, d_{ach}, V_{ach}, X)=w_1F_{ref}(d_{ref}, V_{ref}, X)+w_2F_{further}(d_{ach}, V_{ref}, x)$, where x represents the optimizable parameters, $d_{ref}$ is the reference dose, $V_{ref}$ is the reference volume, $d_{ach}$ is the achieved dose at the reference volume, $V_{ach}$ is the volume that would receive the reference dose, $w_1$ is the weight assigned to the reference objective $F_{ref}$, and $w_2$ is the weight assigned to the further objective $F_{further}$. $w_1$ and $w_2$ may be equal or different.

Additionally and optionally, the further objective comprises the same cost function as the reference objective.

Additionally and optionally, step 3033 is performed responsive to the achieved dose at the reference volume or the achieved volume at the reference dose not meeting the reference objective. By not meeting the reference objective, it is meant the achieved dose at the reference volume or the achieved volume at the reference dose deviates from the reference objective by a predetermined amount. In particular, it is meant that the achieved dose at the reference volume deviates from the reference dose or that the achieved volume at the reference dose deviates from the reference volume by a predetermined amount. Yet optionally, in response to the achieved dose at the reference volume and/or the achieved volume at the reference dose meeting the reference objective, step 3033 is omitted. At step 304, a treatment plan is generated using the optimised set of parameters from step 3031 (instead of the further optimised set of parameters from step 3033).

Additionally and optionally, in relation to step 3033, responsive to the achieved dose at the reference volume and/or the achieved volume at the reference dose not meeting the reference objective, the achieved dose at the reference volume is modified to obtain a relaxed dose. The further objective of step 3033 is then based on the relaxed dose at the reference volume. Optionally, the further objective is based on the achieved volume at the reference dose, together with the relaxed dose at the reference volume. Modifying the achieved dose to obtain a relaxed dose has the same meaning as described in relation to FIG. 2.

Example scenario—An example of a scenario according to FIG. 3 is described next. In an example, the reference objective is to achieve a dose of 60 Gy in 99.5% of the volume of a target. After optimisation according to the reference objective (step 3031), it is determined that a dose of 52 Gy is achieved in 99.5% of the volume (achieved dose at reference volume). It is also found that 80% of the volume of the target would receive the reference dose of 60 Gy (achieved volume at reference dose). Further optimisation (step 3033) is then performed according to the reference objective and a further objective based on 52 Gy in 99.5% of the volume (achieved dose at reference volume) and/or 60 Gy in 80% of the target volume (achieved volume at reference dose). A further optimised set of parameters is obtained, and a treatment plan is generated from those parameters.

Figure 4:
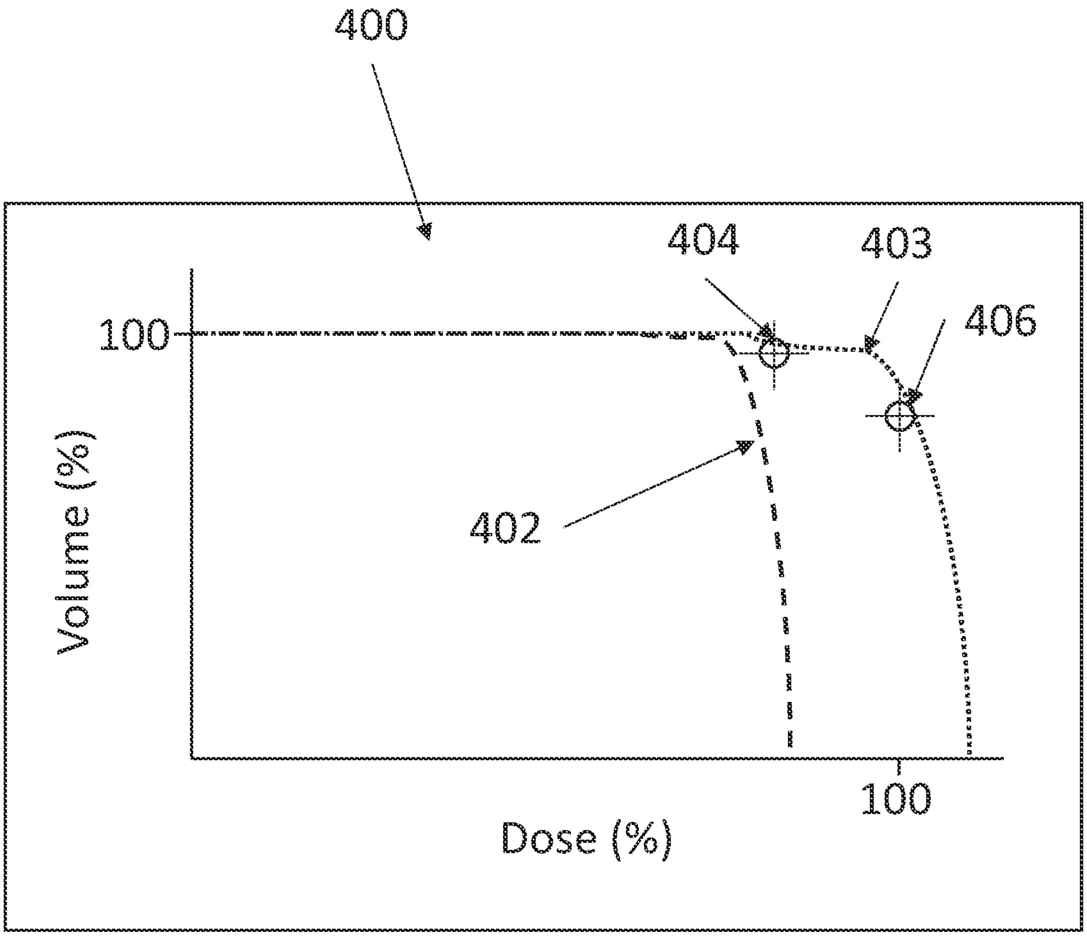
FIG. 4 shows an example of a dose-volume histogram (DVH) for a target.

FIG. 4 shows an illustration of a dose-volume histogram (DVH) 400 for a target. As described herein, a DVH relates the radiation dose to a volume of an anatomical structure. DVHs may be used to evaluate and compare generated treatment plans. The vertical axis represents the fraction of the volume of the anatomical structure (target in this figure) and is represented as a percentage. The horizontal axis represents the dose. In FIG. 4, the horizontal axis is normalised to the prescribed dose (reference objective) and is shown as a percentage (however, absolute units of Gy may be used instead). The DVH 400 shows two curves 402 and 403. Curves 402 and 403 will be described by reference to the scenario described in relation to FIG. 2, namely that the first reference objective is to obtain a dose of 60 Gy in 99.5% of the of the volume of the target. The second reference objective may relate to a different treatment planning objective. For example, the second reference objective may relate to keeping the dose in an OAR to a minimum. Thus, there may be a trade-off between meeting the first reference objective, which seeks to increase dose in a target, and meeting the second reference objective, which seeks to reduce dose in an OAR.

In an ideal scenario, the DVH curve for the target would be square shaped (i.e., 100% of the volume would achieve 100% of the prescribed dose of 60 Gy).

Curve 402 (shown by dashed lines - - - ) represents a comparative example where optimisation is performed as follows. A first optimisation procedure is performed according to the first reference objective, and then a second optimisation is performed according to the second reference objective. Curve 402 lies to the left of the 100% dose (i.e. 60 Gy) in 100% of the target volume. This indicates that no portion of the target volume would obtain the reference dose of 60 Gy (i.e. 100% on the horizontal axis).

Curve 403 (shown by dotted lines . . . ) relates to the outcome when the method of FIG. 2 is used. Part of the curve lies to the right of the 100% dose (i.e. 60 Gy) in 100% of the target volume, which indicates that at least a fraction of the target volume would receive the prescribed dose. The outcome represented by curve 403 may be more desirable than the outcome depicted by curve 402.

Part 404 represents the dose that would be received by 99.5% of the target volume (i.e., the achieved dose at the reference volume). Part 406 represents the volume that would receive 100 percent of the prescribed dose of 60 Gy (i.e., the achieved volume at reference dose). In the example scenario described in relation to FIG. 2, point 404 corresponds to the 52 Gy in 99.5% of the target volume, and point 406 corresponds to the 60 Gy in 80% of the target volume. By using point 406 (and alternatively or additionally, point 404) as a constraint in the optimisation according to the second reference objective, the optimiser is pushed to find solutions that meet those constraints. This may lead to a more desirable treatment plan (as illustrated by curve 403 in FIG. 4).

Curve 403 may also relate to the outcome when the method of FIG. 3 is used. In this case, a further objective based on point 406 (and optionally 404), influences the optimiser towards solutions that may meet the further objective.

Figure 5:
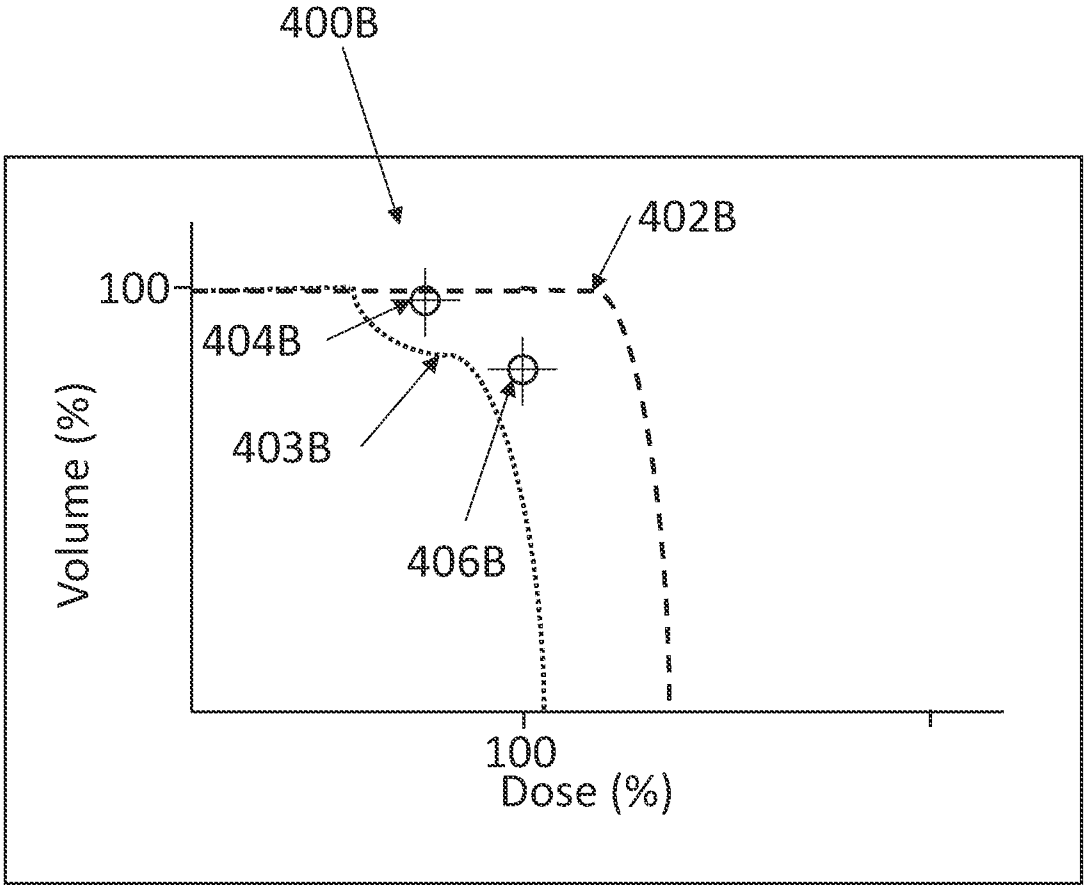
FIG. 5 shows an example of a dose-volume histogram (DVH) for an OAR.

FIG. 5 shows an illustration of a dose-volume histogram (DVH) 400B for an OAR. DVH 400B is analogous to DVH 400 of FIG. 4 except that is it relates to an OAR, where the aim is to reduce the dose received by the OAR. Curve 402B and 403B correspond to curves 402 and 403 respectively. In DVH 400B, 100% dose on the horizontal axis represents an upper limit on the dose to delivered. Points 404B and 406B correspond to points 404 and 406 of FIG. 4. Curve 402B lies to the right of the 100% dose at the 100% volume point (undesirable) while at least part of curve 403B lies to the left of the 100% dose at the 100% volume point.

In more detail, curve 402B (shown by dashed lines - - - ) represents a comparative example where optimisation is performed as follows. A first optimisation procedure is performed according to the first reference objective (where the aim is to reduce the dose to an OAR), and then a second optimisation is performed according to the second reference objective (where the aim may be to increase dose at a different structure). Curve 402B lies to the right of the 100% dose at around 100% of the target volume. This indicates that most of the volume of the OAR would obtain an excessive dose.

Curve 403B (shown by dotted lines . . . ) relates to the outcome when the method of FIG. 2 is used. Part of the curve lies to the left of the 100% dose (i.e., under the upper dose limit) for some of the volume of the anatomical structure. Curve 403B may be more desirable than curve 402B An example of a wish-list is described next in relation to Table 1. A wish-list represents the clinical prescription. The clinical prescription may be defined by a user and defines what is desired to be achieved. A wish-list comprises one or more objectives. Here, the objective corresponds to reference objective 104, 201, or 301 described herein. Alternatively (not shown in table 1), the objective may be formulated as a constraint instead. The constraint refers to the constraint 105 described herein.

An example of part of a wish-list for radiotherapy of prostate cancer is described below.

TABLE 1

Example of a wish-list

| | Clinical & Planning Constraints | | | | |
|---|---|---|---|---|---|
| row | Type | Layering order | Structure | Cost function (parameter values) | Goal |
| a | Clinical | 5 | External | Max Dose | <38 Gy |
| b | Clinical | 6 | Rectum | Parallel (32 Gy, k = 4) | <4.5% |

TABLE 1-continued

| Example of a wish-list | | | | | |
|---|---|---|---|---|---|
| C | Clinical | 6 | Rectum | Parallel (28 Gy, k = 4) | <9.5% |
| d | Clinical | 6 | Rectum | Parallel (18 Gy, k = 4) | <34.5% |
| e | Clinical | 8 | Femoral head right | Maximum Dose | <19 Gy |
| f | Clinical | 9 | Femoral head left | Maximum Dose | <19 Gy |
| g | Planning | 1 | Urethral PRV | Quadratic Overdose (35 Gy) | <0.05 Gy |
| | Planning | 2 | PTV rectum | Quadratic Overdose (34.5 Gy) | <0.10 Gy |
| | Planning | 3 | PTV bladder | Quadratic Overdose (34.5 Gy) | <0.04 Gy |
| | Planning | 4 | PTV | Quadratic Overdose (37.3 Gy) | <0.02 Gy |
| k | Planning | 5 | External | Quadratic Overdose (32 Gy) | <0.09 Gy |
| l | Planning | 5 | External | Quadratic Overdose (11.5 Gy) | <0.02 Gy |

| | Prioritised Objectives | | | | |
|---|---|---|---|---|---|
| | Priority | Layering order | Structure | Cost function (parameter values) | Goal |
| m | 1 | 1 | Urethral PRV(a) | Target Penalty (97%) | >33.2 Gy |
| n | 1 | 2 | PTV rectum | Target Penalty (97%) | >33.2 Gy |
| o | 1 | 3 | PTV bladder | Target Penalty (95%) | >33.2 Gy |
| p | 1 | 4 | PTV | Target Penalty (97%) | >35 Gy |
| q | 1 | 4 | PTV | Target Penalty (99.5%) | >33.2 Gy |
| r | 2 | 6 | Rectum | Parallel (28 Gy, k = 4) | <1% |
| S | 3 | 6 | Rectum | Serial (k = 1) | <10% |
| t | 4 | 6 | Rectum | Parallel (18 Gy, k = 4) | <20% |
| u | 5 | 7 | Bladder | Serial (k = 1) | <12 Gy |
| v | 7 | 10 | Penile bulb | Serial (k = 1) | <2 Gy |
| w | 8 | 8 | Femoral head right | Quadratic Overdose (15 Gy) | <0.5 Gy |
| x | 8 | 9 | Femoral head left | Quadratic Overdose (15 Gy) | <0.5 Gy |

The wish-list shown in Table 1 comprises the following.

The wish-list comprises the 'clinical' constraints (rows a to f). The violation of those constraints implies plan rejection. The wish-list further comprises 'planning' constraints (rows g to l). The purpose of 'planning' constraints is to achieve dose conformality and control of potential hotspots.

The clinical constraints and planning constraints are predefined constraints. For example, step 407 of FIG. 4 may refer to checking whether such clinical constraints are met. The purpose of constraints in rows a to I is to limit the dose at the corresponding structures.

In Table 1, the structure name represents an anatomical structure. The structures are obtained by a process known as segmentation, where contours are drawn on a slice of an MRI image or a CT image to identify the different structures. The contour may be generated manually (e.g., by a physician, dosimetrist, or health care worker) or automatically using an Atlas-based auto-segmentation software.

The wish-list further comprises prioritised objectives (row m to x). The prioritised objectives correspond to the reference objective described herein. The prioritized objectives comprise: objectives that relate to the dose coverage and conformality of the target (which are the 1st-priority objectives in rows m to q), and objectives that are concerned with dose sparing of the OARs (rows r to y). The prioritised objective may be user-defined priorities.

In Table 1, the "Cost function (parameter values)" relates to the type of cost function to be used. For some cost functions, additional parameters are provided. The 'Goal' refers to a dose or volume to be achieved by the treatment planning system.

For example, at row m, the reference objective is for 97% of the Urethral PRV (a) to achieve a dose of 33.2 Gy. The cost function associated to said reference objective is a 'Target Penalty'.

For each structure, one or more cost functions and associated goals, each achieving different purposes, is defined. For example, at rows r to t, for the 'Rectum' structure, different cost functions and goals are applied.

In Table 1, the priority refers to the relative priority of the reference objectives. In table 1, the objectives that relate to dose coverage and conformality of the target (which are the 1st-priority objectives in rows m to q) are optimised first, and objectives that are concerned with dose sparing of the OARs (rows r to y) are optimised after, in order of their priorities.

In table 1, the layering order relates to structure volumes that overlap. When structures comprise overlapping voxels, the structure with the higher layering order 'owns' the voxel.

A further example of a wish-list is provided in Naccarato, S., Rigo, M., Pellegrini, R., Voet, P., Akhiat, H., Gurrera, D., De Simone, A., Sicignano, G., Mazzola, R., Figlia, V. and Ricchetti, F., 2022. Automated planning for prostate stereotactic body radiation therapy on the 1.5 T MR-Linac. Advances in radiation oncology, 7(3), p. 100865.

Figure 6:
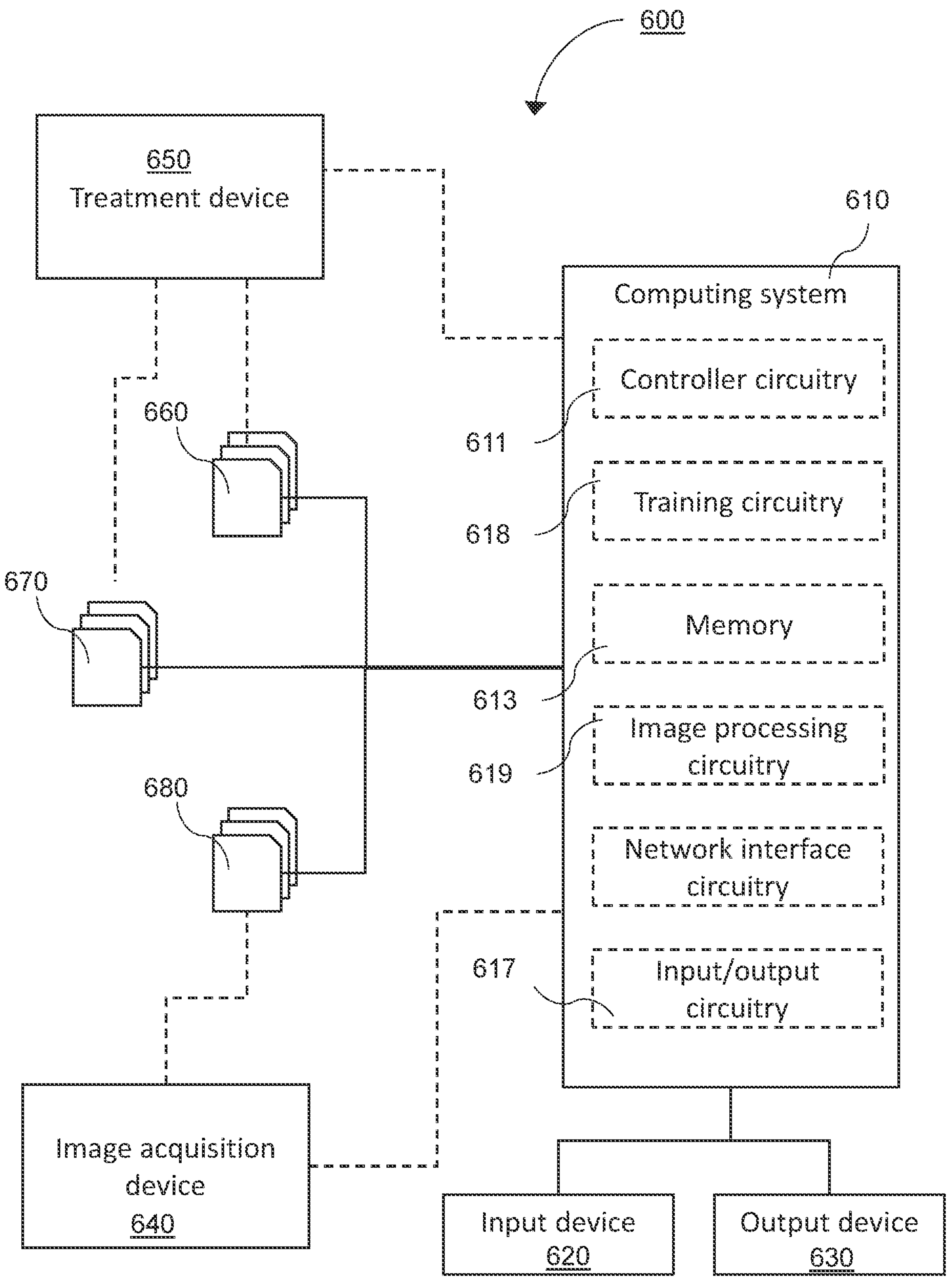
FIG. 6 shows a schematic illustration of a radiotherapy system according to an embodiment.
Figure 7:
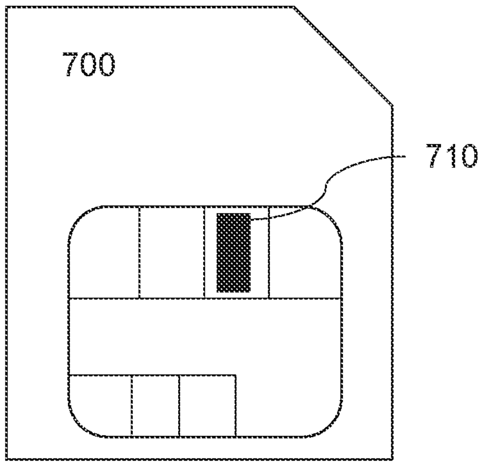
FIG. 7 shows a schematic illustration of a computer-readable medium according to an embodiment.

FIG. 6 illustrates a block diagram of an implementation of a radiotherapy system 600. The radiotherapy system 600 comprises a computing system 610 within which a set of instructions, for causing the computing system 610 to perform any one or more of the methods discussed herein, may be executed. The computing system 610 may implement a treatment planning system. The computing system 610 may also be referred to as a computer. The treatment planning system 610 may perform any of the methods described herein. In particular, the methods described herein may be implemented by a processor 611 of the treatment planning system 610.

The computing system 610 shall be taken to include any number or collection of machines, e.g. computing device(s), that individually or jointly execute a set (or multiple sets) of instructions to perform any one or more of the methods discussed herein. That is, hardware and/or software may be provided in a single computing device, or distributed across a plurality of computing devices in the computing system. In some implementations, one or more elements of the computing system may be connected (e.g., networked) to other machines, for example in a Local Area Network (LAN), an intranet, an extranet, or the Internet. One or more elements of the computing system may operate in the capacity of a server or a client machine in a client-server network environment, or as a peer machine in a peer-to-peer (or distributed) network environment. One or more elements of the computing system may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

The computing system 610 includes controller circuitry 611 and a memory 613 (e.g., read-only memory (ROM), flash memory, dynamic random access memory (DRAM) such as synchronous DRAM (SDRAM) or Rambus DRAM (RDRAM), etc.). The memory 613 may comprise a static memory (e.g., flash memory, static random access memory (SRAM), etc.), and/or a secondary memory (e.g., a data storage device), which communicate with each other via a bus (not shown).

Controller circuitry 611 represents one or more general-purpose processors such as a microprocessor, central processing unit, accelerated processing units, or the like. More particularly, the controller circuitry 611 may comprise a complex instruction set computing (CISC) microprocessor, reduced instruction set computing (RISC) microprocessor, very long instruction word (VLIW) microprocessor, processor implementing other instruction sets, or processors implementing a combination of instruction sets. Controller circuitry 611 may also include one or more special-purpose processing devices such as an application specific integrated circuit (ASIC), a field programmable gate array (FPGA), a digital signal processor (DSP), network processor, or the like. One or more processors of the controller circuitry may have a multicore design. Controller circuitry 611 is configured to execute the processing logic for performing the operations and steps discussed herein.

The computing system 610 may further include a network interface circuitry 618. The computing system 610 may be communicatively coupled to an input device 620 and/or an output device 630, via input/output circuitry 617. In some implementations, the input device 620 and/or the output device 630 may be elements of the computing system 610. The input device 620 may include an alphanumeric input device (e.g., a keyboard or touchscreen), a cursor control device (e.g., a mouse or touchscreen), an audio device such as a microphone, and/or a haptic input device. The output device 630 may include an audio device such as a speaker, a video display unit (e.g., a liquid crystal display (LCD) or a cathode ray tube (CRT)), and/or a haptic output device. In some implementations, the input device 620 and the output device 630 may be provided as a single device, or as separate devices.

In some implementations, the computing system 610 may comprise image processing circuitry 619. Image processing circuitry 619 may be configured to process image data 680 (e.g. images, or imaging data), such as medical images obtained from one or more imaging data sources, a treatment device 650 and/or an image acquisition device 640. Image processing circuitry 619 may be configured to process, or pre-process, image data. For example, image processing circuitry 619 may convert received image data into a particular format, size, resolution or the like. In some implementations, image processing circuitry 619 may be combined with controller circuitry 611.

Figure 8:
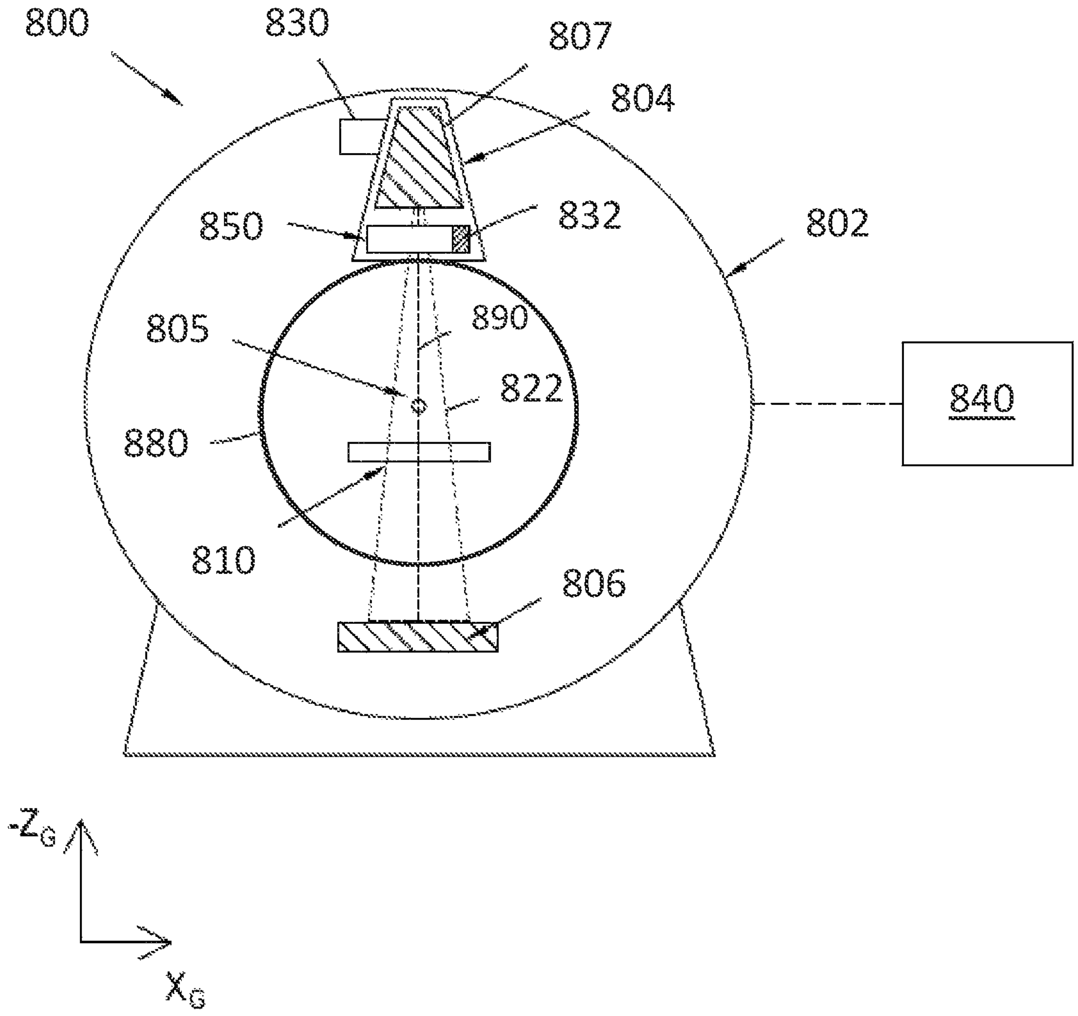
FIG. 8 shows a radiotherapy device or apparatus.

In some implementations, the radiotherapy system 600 may further comprise an image acquisition device 640 and/or a treatment device 650, such as those disclosed herein in the examples of FIG. 8. The image acquisition device 640 and the treatment device 650 may be provided as a single device. In some implementations, treatment device 650 is configured to perform imaging, for example in addition to providing treatment and/or during treatment. The treatment device 650 comprises the main radiation delivery components of the radiotherapy system, such as beam shaping apparatus 850.

Image acquisition device 640 may be configured to perform positron emission tomography (PET), computed tomography (CT), magnetic resonance imaging (MRI), single positron emission computed tomography (SPECT), x-ray, and the like.

Image acquisition device 640 may be configured to output image data 680, which may be accessed by computing system 610. Treatment device 650 may be configured to output treatment data 660, which may be accessed by computing system 610.

Computing system 610 may be configured to access or obtain treatment data 660, planning data 670 and/or image data 680. Treatment data 660 may be obtained from an internal data source (e.g. from memory 613) or from an external data source, such as treatment device 650 or an external database. Planning data 670 may be obtained from memory 613 and/or from an external source, such as a planning database. Planning data 670 may comprise information obtained from one or more of the image acquisition device 640 and the treatment device 650.

The various methods described above may be implemented by a computer program. The computer program may include computer code (e.g. instructions) 710 arranged to instruct a computer to perform the functions of one or more of the various methods described above. For example, the steps of the methods described in relation to FIG. 2, and FIG. 3 may be performed by the computer code 710. The steps of the methods described above may be performed in any suitable order. The computer program and/or the code 710 for performing such methods may be provided to an apparatus, such as a computer, on one or more computer readable media or, more generally, a computer program product 700)), depicted in FIG. 8. The computer readable media may be transitory or non-transitory. The one or more computer readable media 700 could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD. The instructions 710 may also reside, completely or at least partially, within the memory 613 and/or within the controller circuitry 611 during execution thereof by the computing system 610, the memory 613 and the controller circuitry 611 also constituting computer-readable storage media.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may comprise a special-purpose processor, such as an FPGA or an ASIC. A hardware component may also include programmable logic or circuitry that is temporarily configured by software to perform certain operations.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

FIG. 8 depicts a radiotherapy apparatus according to the present disclosure. FIG. 8 shows a cross-section through a radiotherapy apparatus 800 comprising a radiation head 804 and a beam receiving apparatus 806, both of which are attached to a gantry 802. The radiation head 804 includes a radiation source 807 which emits a beam of radiation 822. The radiation head 804 also includes a beam shaping apparatus 850 which controls the size and shape of the radiation field associated with the beam.

The beam receiving apparatus 806 is configured to receive radiation emitted from the radiation head 804, for the purpose of absorbing and/or measuring the beam of radiation. In the view shown in FIG. 8, the radiation head 804 and the beam receiving apparatus 806 are positioned diametrically opposed to one another.

The gantry 802 is rotatable, and supports the radiation head 804 and the beam receiving apparatus 806 such that they are rotatable around an axis of rotation 805, which may coincide with the patient longitudinal axis. As shown in FIG. 8, the gantry provides rotation of the radiation head 804 and the beam receiving apparatus 806 in a plane which is perpendicular to the patient longitudinal axis (e.g. a sagittal plane). Three gantry directions XG, YG, ZG can be defined, where the YG direction is perpendicular with gantry axis of rotation. The ZG direction extends from a point on the gantry corresponding to the radiation head, towards the axis of rotation of the gantry. Therefore, from the patient frame of reference, the ZG direction rotates around as the gantry rotates.

FIG. 8 also shows a support surface 810 on which a subject (or patient) is supported during radiotherapy treatment. The radiation head 804 is configured to rotate around the axis of rotation 805 such that the radiation head 804 directs radiation towards the subject from various angles around the subject in order to spread out the radiation dose received by healthy tissue to a larger region of healthy tissue while building up a prescribed dose of radiation at a target region.

The radiotherapy apparatus 800 is configured to deliver a radiation beam towards a radiation isocentre which is substantially located on the axis of rotation 805 at the centre of the gantry 802 regardless of the angle at which the radiation head 804 is placed.

The rotatable gantry 802 and radiation head 804 are dimensioned so as to allow a central bore 880 to exist. The central bore 880 provides opening sufficient to allow a subject to be positioned therethrough without the possibility of being incidentally contacted by the radiation head 804 or other mechanical components as the gantry rotates the radiation head 804 about the subject.

As shown in FIG. 8, the radiation head 804 emits the radiation beam 822 along a beam axis 890 (or radiation axis or beam path), where the beam axis 890 is used to define the direction in which the radiation is emitted by the radiation head. The radiation beam 822 is incident on the beam receiving apparatus 806 which can include at least one of a beam stopper and a radiation detector. The beam receiving apparatus 806 is attached to the gantry 802 on a diametrically opposite side to the radiation head 804 to attenuate and/or detect a beam of radiation after the beam has passed through the subject.

The radiation beam axis 890 may be defined as, for example, a centre of the radiation beam 822 or a point of maximum intensity.

The beam shaping apparatus 850 delimits the spread of the radiation beam 822. The beam shaping apparatus 850 is configured to adjust the shape and/or size of a field of radiation produced by the radiation source. The beam shaping apparatus 850 does this by defining an aperture (also referred to as a window or an opening) of variable shape to collimate the radiation beam 822 to a chosen cross-sectional shape. In this example, the beam shaping apparatus 850 may be provided by a combination of a diaphragm and a multi-leaf collimator (MLC). Beam shaping apparatus 850 may also be referred to as a beam modifier.

The radiotherapy apparatus 800 may be configured to deliver both coplanar and non-coplanar (also referred to as tilted) modes of radiotherapy treatment. In coplanar treatment, radiation is emitted in a plane which is perpendicular to the axis of rotation of the radiation head 804. In non-coplanar treatment, radiation is emitted at an angle which is not perpendicular to the axis of rotation. In order to deliver coplanar and non-coplanar treatment, the radiation head 804 can move between at least two positions, one in which the radiation is emitted in a plane which is perpendicular to the axis of rotation (coplanar configuration) and one in which radiation is emitted in a plane which is not perpendicular to the axis of rotation (non-coplanar configuration).

In the coplanar configuration, the radiation head is positioned to rotate about a rotation axis and in a first plane. In the non-coplanar configuration, the radiation head is tilted with respect to the first plane such that a field of radiation produced by the radiation head is directed at an oblique angle relative to the first plane and the rotation axis. In the non-coplanar configuration, the radiation head is positioned to rotate in a respective second plane parallel to and displaced from the first plane. The radiation beam is emitted at an oblique angle with respect to the second plane, and therefore as the radiation head rotates the beam sweeps out a cone shape.

The beam receiving apparatus 806 remains in the same place relative to the rotatable gantry when the radiotherapy apparatus is in both the coplanar and non-coplanar modes. Therefore, the beam receiving apparatus 806 is configured to rotate about the rotation axis in the same plane in both coplanar and non-coplanar modes. This may be the same plane as the plane in which the radiation head rotates.

The beam shaping apparatus 850 is configured to reduce the spread of the field of radiation in the non-coplanar configuration in comparison to the coplanar configuration.

The radiotherapy apparatus 800 includes a controller 840 which is programmed to control the radiation source 807, beam receiving apparatus 806 and the gantry 802. Controller 840 may perform functions or operations such as treatment planning, treatment execution, image acquisition, image processing, motion tracking, motion management, and/or other tasks involved in a radiotherapy process.

Controller 840 is programmed to control features of apparatus 800 according to a radiotherapy treatment plan for irradiating a target region, also referred to as a target tissue, of a patient. The treatment plan includes information about a particular dose to be applied to a target tissue, as well as other parameters such as beam angles, dose-histogram-volume information, the number of radiation beams to be used during therapy, the dose per beam, and the like. Controller 840 is programmed to control various components of apparatus 800, such as gantry 802, radiation head 804, beam receiving apparatus 806, and support surface 810, according to the treatment plan.

Hardware components of controller 840 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 840 may include operation device software, application software, etc.

The radiation head 804 may be connected to a head actuator 830 which is configured to actuate the radiation head 804, for example between a coplanar configuration and one or more non-coplanar configurations. This may involve translation and rotation of the radiation head 804 relative to the gantry. In some implementations, the head actuator may include a curved rail along which the radiation head 804 may be moved to adjust the position and angle of the radiation head 804. The controller 840 may control the configuration of the radiation head 804 via the head actuator 830.

The beam shaping apparatus 850 includes a shaping actuator 832. The shaping actuator is configured to control the position of one or more elements in the beam shaping apparatus 850 in order to shape the radiation beam 822. In some implementations, the beam shaping apparatus 850 includes an MLC, and the shaping actuator 832 includes means for actuating leaves of the MLC. The beam shaping apparatus 850 may further comprise a diaphragm, and the shaping actuator 832 may include means for actuating blocks of the diaphragm. The controller 840 may control the beam shaping apparatus 850 via the shaping actuator 832.

A treatment plan may comprise positioning information of beam shaping apparatus 850. The positioning information of beam shaping apparatus 850 may comprise information indicating a configuration of one or more elements of beam shaping apparatus 850, such as leaf configuration of an MLC of beam shaping apparatus 850, a configuration of a diaphragm of beam shaping apparatus 850, a configuration of an opening (e.g., window or aperture) of the MLC, and/or the like.

Additional Notes

As described herein, the purpose of an optimiser (or of an optimisation procedure) is to find a set of optimised parameters for which a cost function is minimised. However, it will be understood that, alternatively and equivalently, the purpose of the optimiser (or of the optimisation procedure) may be taken to be to find a set of optimised parameters for which a reward function is maximised.

As described herein, a dose-volume metric comprises a dose value and a corresponding volume value. The dose value and the corresponding volume value may be obtained from a dose distribution that would be achieved in the anatomical structure. The dose-volume metric for an anatomical structure indicates how much (i.e. what volume) of the anatomical structure receives a certain dose. The dose-volume metric may be a certain dose that would be received by a certain volume of the anatomical structure. More particularly, as described above, the dose-volume metric may be (i) the dose that would be received by a prescribed volume of an anatomical structure (achieved dose at the reference volume), and/or (ii) the volume of an anatomical structure would actually receive a prescribed dose (achieved volume at the reference dose). It will be understood that, alternatively, the dose-volume metric may be (a) the dose would be received by a volume that is between 70% to 100% of the prescribed volume of an anatomical structure (achieved dose at a volume that is 70%-100% of the reference volume), and/or (b) the volume of an anatomical structure would receive a dose that is 80% to 120% of the prescribed dose (achieved volume at a dose that is 80%-120% of the reference dose). In other examples, the dose-volume metric may be the dose would be received by a volume that is between 80% to 100% or between 90% to 100% of the prescribed volume of an anatomical structure, and/or the volume of an anatomical structure would receive a dose that is 90% to 110% of the prescribed dose.

Unless specifically stated otherwise, as apparent from the following discussion, it is appreciated that throughout the description, discussions utilizing terms such as "receiving", "determining", "comparing", "enabling", "maintaining," "identifying,", "obtaining", "accessing" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While certain embodiments have been described, these embodiments have been presented by way of example only, and are not intended to limit the scope of the present disclosure. Indeed, the novel methods and apparatus described herein may be embodied in a variety of other forms; furthermore, various omissions, substitutions and changes in the form of methods and apparatus described herein may be made.

EXAMPLES

Aspects and features of the present disclosure are set forth in the following numbered clauses:

Clause 1. A method of radiation treatment planning for a radiotherapy system, the method comprising:

receiving a first reference objective and a second reference objective, each reference objective representing a goal to be achieved by the radiotherapy system, and the first reference objective comprising a reference dose to be delivered to a reference volume of an anatomical structure, optimising a set of parameters, according to the received first reference objective and the received second reference objective, the set of parameters relating to characteristics of radiation to be delivered by the radiotherapy system, wherein optimising the set of parameters comprises:

optimising the set of parameters based on the first reference objective to obtain a dose-volume metric for the anatomical structure, and further optimising the set of parameters based on the second reference objective using the dose-volume metric as constraint, and generating a radiation treatment plan using the further optimised set of parameters.

Clause 2. The method of clause 1, wherein the dose-volume metric comprises an achieved dose at a volume that is between 70% to 100% of the reference volume, and/or an achieved volume at a dose that is between 80% to 120% of the reference dose.

Clause 3. The method of clause 1 or 2, wherein the dose-volume metric comprises an achieved dose at the reference volume, and/or an achieved volume at the reference dose.

Clause 4. The method according to any preceding clauses wherein optimising the set of parameters comprises:

responsive to the dose-volume metric not meeting the first reference objective, further optimising the set of parameters based on the second reference objective using the dose-volume metric as constraint.

Clause 5. The method of clause 4, when dependent on clause 3, wherein optimising the set of parameters comprises:

responsive to the achieved dose at the reference volume and/or the achieved volume at the reference dose not meeting the first reference objective, modifying the achieved dose at the reference volume to obtain a relaxed dose, and further optimising the set of parameters based on the second reference objective using the relaxed dose at the reference volume as constraint.

Clause 6. The method according to any preceding clause, wherein obtaining the dose-volume metric from the optimised set of parameters comprises:

obtaining a dose distribution in the anatomical structure using the optimised set of parameters, and obtaining the dose-volume metric from the dose distribution.

Clause 7. The method of clause 6, wherein the dose distribution is represented by a dose-volume histogram, DVH.

Clause 8. The method of according to any preceding clause, wherein the first reference objective comprises any one of the following cost functions: a Target Penalty cost function; an Underdose DVH cost function, an Overdose DVH cost function, and a Parallel cost function.

Clause 9. The method of clause 8, wherein the constraint used in the further optimisation comprise the same cost function as the first reference objective.

Clause 10. The method according to any preceding clause, wherein optimising the set of parameters comprises:

optimising the set of parameters based on the first reference objective to obtain the dose-volume metric, and further optimising the set of parameters, using the dose-volume metric as an objective, to obtain an intermediate set of parameters, further optimising the intermediate set of parameters, based on the second reference objective and using the dose-volume metric as a constraint, to obtain the further optimised set of parameters.

Clause 11. The method of clause 10, wherein the dose-volume metric comprises an achieved volume at the reference dose and/or an achieved dose at the reference volume, and wherein further optimising the set of parameters, using the dose-volume metric as objective, comprises using a weighted sum of a first cost function based on the achieved volume at the reference dose and a second cost function based on the achieved dose at the reference volume.

Clause 12. A method of radiation treatment planning for a radiotherapy system, the method comprising:

receiving a reference objective, the reference objective representing a goal to be achieved by the radiotherapy system, the reference objective comprising a reference dose to be delivered to a reference volume of an anatomical structure, optimising a set of parameters, according to the received reference objective, the set of parameters relating to characteristics of radiation to be delivered by the radiotherapy system, wherein optimising the set of parameters comprises:

optimising the set of parameters based on the reference objective to obtain a dose-volume metric, and further optimising the set of parameters, based on the received reference objective and a further objective that is based on the dose-volume metric, generating a radiation treatment plan using the further optimised set of parameters.

Clause 13. The method of clause 12, wherein the dose-volume metric comprises an achieved volume at the reference dose and/or an achieved dose at the reference volume.

Clause 14. The method of clause 12 or 13, wherein further optimising the set of parameters, comprises using a cost function based on a weighted sum of the reference objective and the further objective.

Clause 15. A computer-readable medium comprising computer-executable instructions configured to cause a processor to perform any of the preceding clauses.

Clause 16. A radiation treatment planning system comprising a processor configured to:

receive a first reference objective and a second reference objective, each reference objective representing a goal to be achieved by the radiotherapy system, and the first reference objective comprising a reference dose to be delivered to a reference volume of an anatomical structure, optimise a set of parameters, according to the received first reference objective and the received second reference objective, the set of parameters relating to characteristics of radiation to be delivered by the radiotherapy system, wherein optimising the set of parameters comprises:

optimising the set of parameters based on the first reference objective to obtain a dose-volume metric, and further optimising the set of parameters based on the second reference objective using the dose-volume metric as constraint, generate a radiation treatment plan using the further optimised set of parameters.

Clause 17. The treatment planning system of clause 16, wherein the processor is configured to perform any of the methods above.

Clause 18. A radiation treatment planning system comprising a processor configured to:

receive a reference objective, the reference objective representing a goal to be achieved by the radiotherapy system, the reference objective comprising a reference dose to be delivered to a reference volume of an anatomical structure, optimise a set of parameters, according to the received reference objective, the set of parameters relating to characteristics of radiation to be delivered by the radiotherapy system, wherein optimising the set of parameters comprises:

optimising the set of parameters based on the reference objective to obtain a dose-volume metric, and further optimising the set of parameters, based on the received reference objective and a further objective that is based on the dose-volume metric, generate a radiation treatment plan using the further optimised set of parameters.

Clause 19. The treatment planning system of clause 18, wherein the processor is configured to perform any of the methods above.

What is claimed is:

1. A computer-implemented method of radiation treatment planning for a radiotherapy system, the method comprising:

receiving a first reference objective and a second reference objective, each reference objective representing a goal to be achieved by the radiotherapy system, the first reference objective comprising a reference dose to be delivered to a reference volume of an anatomical structure;

optimizing a set of parameters, according to the received first reference objective and the received second reference objective, the set of parameters relating to characteristics of radiation to be delivered by the radiotherapy system, wherein optimizing the set of parameters comprises:

optimizing the set of parameters based on the first reference objective to obtain a dose-volume metric for the anatomical structure, wherein the dose-volume metric comprises an achieved volume at the reference dose and an achieved dose at the reference volume;

further optimizing the set of parameters based on the second reference objective using the dose-volume metric as a constraint;

further optimizing the set of parameters, using the dose-volume metric as an objective, to obtain an intermediate set of parameters, by using a weighted sum of a first cost function based on the achieved volume at the reference dose and a second cost function based on the achieved dose at the reference volume; and further optimizing the intermediate set of parameters, based on the second reference objective, and using the dose-volume metric as a constraint, to obtain the further optimized set of parameters;

generating a radiation treatment plan using the further optimized set of parameters;

outputting the radiation treatment plan to the radiotherapy system; and causing radiation therapy to be delivered to a patient by the radiotherapy system according to the radiation treatment plan.

2. The method of claim 1, wherein the dose-volume metric comprises an achieved dose at a volume that is between 70% to 100% of the reference volume, and/or an achieved volume at a dose that is between 80% to 120% of the reference dose.

3. The method of claim 1, wherein the dose-volume metric comprises an achieved dose at the reference volume, and/or an achieved volume at the reference dose.

4. The method according to claim 1 wherein optimizing the set of parameters comprises:

responsive to the dose-volume metric not meeting the first reference objective, further optimizing the set of parameters based on the second reference objective using the dose-volume metric as a constraint.

5. The method of claim 3, wherein optimizing the set of parameters comprises:

responsive to the achieved dose at the reference volume and/or the achieved volume at the reference dose not meeting the first reference objective, modifying the achieved dose at the reference volume to obtain a relaxed dose; and further optimizing the set of parameters based on the second reference objective using the relaxed dose at the reference volume as a constraint.

6. The method according to claim 1, wherein obtaining the dose-volume metric from the optimized set of parameters comprises:

obtaining a dose distribution in the anatomical structure using the optimized set of parameters; and obtaining the dose-volume metric from the dose distribution.

7. The method of claim 6, wherein the dose distribution is represented by a dose-volume histogram, DVH.

8. The method of claim 1, wherein the first reference objective comprises any one of the following cost functions: a target penalty cost function; an underdose dose-volume histogram (DVH) cost function, an overdose DVH cost function, and a parallel cost function.

9. The method of claim 8, wherein the constraint used in the further optimization comprise the same cost function as the first reference objective.

10. A non-transitory computer-readable medium comprising computer-executable instructions configured to cause a processor to:

receive a first reference objective and a second reference objective, each reference objective representing a goal to be achieved by a radiotherapy system, and the first reference objective comprising a reference dose to be delivered to a reference volume of an anatomical structure;

optimize a set of parameters, according to the received first reference objective and the received second reference objective, the set of parameters relating to characteristics of radiation to be delivered by the radiotherapy system, wherein optimizing the set of parameters comprises:

optimizing the set of parameters based on the first reference objective to obtain a dose-volume metric, wherein the dose-volume metric comprises an achieved volume at the reference dose and an achieved dose at the reference volume;

further optimizing the set of parameters based on the second reference objective using the dose-volume metric as a constraint;

further optimizing the set of parameters, using the dose-volume metric as an objective, to obtain an intermediate set of parameters, by using a weighted sum of a first cost function based on the achieved volume at the reference dose and a second cost function based on the achieved dose at the reference volume; and further optimizing the intermediate set of parameters, based on the second reference objective, and using the dose-volume metric as a constraint, to obtain the further optimized set of parameters;

generate a radiation treatment plan using the further optimized set of parameters;

output the radiation treatment plan to the radiotherapy system; and cause radiation therapy to be delivered to a patient by the radiotherapy system according to the radiation treatment plan.

11. A radiation treatment planning system comprising:

a processor; and memory with instructions stored thereon, which, when executed by the processor, cause the processor to:

receive a first reference objective and a second reference objective, each reference objective representing a goal to be achieved by a radiotherapy system, and the first reference objective comprising a reference dose to be delivered to a reference volume of an anatomical structure;

optimize a set of parameters, according to the received first reference objective and the received second reference objective, the set of parameters relating to characteristics of radiation to be delivered by the radiotherapy system, wherein optimizing the set of parameters comprises:

optimizing the set of parameters based on the first reference objective to obtain a dose-volume metric, wherein the dose-volume metric comprises an achieved volume at the reference dose and an achieved dose at the reference volume;

further optimizing the set of parameters based on the second reference objective using the dose-volume metric as a constraint;

further optimizing the set of parameters, using the dose-volume metric as an objective, to obtain an intermediate set of parameters, by using a weighted sum of a first cost function based on the achieved volume at the reference dose and a second cost function based on the achieved dose at the reference volume; and further optimizing the intermediate set of parameters, based on the second reference objective, and using the dose-volume metric as a constraint, to obtain the further optimized set of parameters;

generate a radiation treatment plan using the further optimized set of parameters;

output the radiation treatment plan to the radiotherapy system; and cause radiation therapy to be delivered to a patient by the radiotherapy system according to the radiation treatment plan.

* * * * *